US006737561B1

(12) United States Patent
Ray et al.

(10) Patent No.: US 6,737,561 B1
(45) Date of Patent: May 18, 2004

(54) GENE ENCODING SHORT INTEGUMENTS AND USES THEREOF

(75) Inventors: Animesh Ray, San Diego, CA (US); Teresa Ann Golden, Pensacola, FL (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/590,968

(22) Filed: Jun. 9, 2000

Related U.S. Application Data

(60) Provisional application No. 60/138,316, filed on Jun. 9, 1999.

(51) Int. Cl.[7] .............................. A01H 1/00; A01H 5/00; C12Q 1/68; C12N 15/88; C07H 2/04
(52) U.S. Cl. ........................ 800/278; 435/6; 435/91.1; 435/458; 536/23.6; 536/24.5; 800/298
(58) Field of Search ..................... 435/6, 69.1, 91.1, 435/468; 536/23.1, 23.6, 24.5; 800/278, 298

(56) References Cited

PUBLICATIONS

JR Ecker, Locus Accession No. AC007323, Apr. 1999.*
Jacobsen et al., "Disruption of an RNA Helicase/RNAse III Gene in Arabidopsis Causes Unregulated Cell Division in Floral Meristems," *Development* 126:5231–5243 (1999).
Alvarez et al., "*Terminal Flower*: A Gene Affecting Inflorescence Development in *Arabidopsis thaliana*," *The Plant J.* 2(1):103–116 (1992).
Amasino, "Control of Flowering Time in Plants," *Curr. Opin. Genet. Dev.* 6:480–487 (1996).
Baker et al., "Interactions Among Genes Regulating Ovule Development in *Arabidopsis thaliana*," *Genetics* 145:1109–1124 (1997).
Berleth et al., "The Role of the monopteros Gene in Organizing the Basal Body Region of the Arabidopsis Embryo," *Development* 118:575–587 (1993).
Cox et al., "A Novel Class of Evolutionarily Class of Evolutionarily Conserved Genes Defined by Piwi are Essential for Stem Cell Self–Renewal," *Genes and Development* 12:3715–3727 (1998).
Bosher, "RNA Interference: Genetic Wand and Genetic Watchdog," *Nature Cell Biol.* 2:E31–E36 (2000).
Chuang et al., "Specific and Heritable Genetic Interference by Double–Stranded RNA in *Arabidopsis thaliana*," *PNAS* 97(9):4985–4990 (2000).
Breitwieser et al., "Oskar Protein Interaction with Vasa Represents an Essential Step in Polar Granule Assembly," *Genes Dev.* 10:2179–2188 (1996).
Broadus et al., "Staufen–Dependent Localization of Prospero mRNA Contributes to Neuroblast Daughter–Cell Fate," *Nature* 391:792–795 (1998).
Castle et al., "Genetic and Molecular Characterization of Embryonic Mutants Identified Following Seed Transformation in Arabidopsis," *Mol. Gen. Genet.* 241:504–514 (1993).
Chanfreau et al., "Yeast RNase III as a Key Processing Enzyme in Small Nucleolar RNAs Metabolism," *J. Mol. Biol.* 284:975–988 (1998).

(List continued on next page.)

Primary Examiner—Ram R. Shukla
Assistant Examiner—Jane Zara
(74) *Attorney, Agent, or Firm*—Nixon Peabody LLP

(57) ABSTRACT

The present invention relates to the isolation and identification of a short integuments protein and the nucleic acid which encodes such protein. The invention also relates to an expression vector containing the encoding nucleic acid and methods whereby plant fertility, fecundity and flowering time are increased or decreased by transformation of plants with that nucleic acid or variants thereof. The present invention also relates to transgenic cells, plants, and seeds containing the short integuments gene of the present invention.

14 Claims, 2 Drawing Sheets

OTHER PUBLICATIONS

Clark et al., "The CLAVATA and Shoot MERISTEMLESS Loci Competitively Regulate Meristem Activity in Arabidopsis," *Development* 122:1565–1575 (1996).

Clark et al., "CLAVATA1, a Regulator of Meristem and Flower Development in Arabidopsis," *Development* 119:397–418 (1993).

Clark et al., "The CLAVATA1 Gene Encodes a Putative Receptor Kinase that Controls Shoot and Floral Meristem Size in Arabidopsis," *Cell* 89:575–585 (1997).

Colombo et al., "Downregulation of Ovule–Specific MADS Box Genes from Petunia Results in Maternally Controlled Defects in Seed Development," *The Plant Cell* 9:703–715 (1997).

Tavernarakis et al., "Heritable and Inducible Genetic Interference by Double–Stranded RNA Encoded by Transgenes," *Nature Genetics* 24:180–183 (2000).

Coupland, "Genetic and Environmental Control of Flowering Time in Arabidopsis," *Trends In Genetics* 11(10):393–397 (1995).

Endrizzi et al., "The Shoot MERISTEMLESS Gene is Required for Maintencance of Undifferentiated Cells in Arabidopsis Shoot and Floral Meristems and Acts at a Different Regulatory Level than the Meristem Genes WUSCHEL and ZWILLE," *The Plant Journal* 10(6):967–979 (1996).

Ferrandon et al., "RNA–RNA Interaction is Required for the Formation of Specific Bicoid mRNA 3' UTR–STUAFEN Ribonucleoprotein Particles," *EMBO J.* 16(7):1751–1758 (1997).

Gaiser et al., "The Arabidopsis Superman Gene Mediates Asymmetric Growth of the Outer Integument of Ovules," *The Plant Cell* 7:333–345 (1995).

Goodrich et al., "A Polycomb–Group Gene Regulates Homeotic Gene Expression in Arabidopsis," *Nature* 386:44–51 (1997).

Grossniklaus et al., "Maternal Control of Embryogenesis by MEDEA, a Polycomb Group Gene in Arabidopsis," *Science* 280:446–450 (1998).

Gustafson–Brown et al., "Regulation of the Arabidopsis Floral Homeotic Gene APETALA1," *Cell* 76:131–143 (1994).

Yang et al., "Genetic Regulation of Shoot Development in Arabidopsis: Role of the EMF Gene," *Developmental Biology* 169:421–435 (1995).

Schneitz et al., "Dissection of Sexual Organ Ontogenesis: A Genetic Analysis of Ovule Development in *Arabidopsis thaliana*," *Development* 124:1367–1376 (1997).

Wickham et al., "Mammalian Staufen is a Double–Stranded–RNA– and Tubulin–Binding Protein Which Localizes to the Rough Endoplasmic Reticulum," *Molecular and Cellular Biology* 19(3):2220–2230 (1999).

Weigel et al., "A Developmental Switch Sufficient for Flower Initiation in Diverse Plants," *Nature* 377:495–500 (1995).

Kagaya et al., "RAV1, a Novel DNA–Binding Protein, Binds to Bipartite Recognition Sequence through Two Distinct DNA–Binding Domains Uniquely Found in Higher Plants," *Nucleic Acids Research* 27(2):470–478 (1999).

Kempin et al., "Molecular Basis of the Cauliflower Phenotype in Arabidopsis," *Science* 267:522–525 (1995).

Weigel et al., "Leafy Controls Floral Meristem Identity in Arabidopsis," *Cell* 69:843–859 (1992).

Weigel, "The Genetics of Flower Development: From Floral Induction to Ovule Morphogenesis," *Ann. Rev. Genet.* 29:19–39 (1995).

Lang et al., "sin1, A Mutation Affecting Female Fertility in Arabidopsis, Interacts With mod1, Its Recessive Modifier," *Genetics* 137:1101–1110 (1994).

Laux et al., "The WUSCHEL Gene is Required for Shoot and Floral Meristem Integrity in Arabidopsis," *Development* 122:87–96 (1996).

Lee et al., "Isolation of LUMINIDEPENDENS: A Gene Involved in the Control of Flowering Time in Arabidopsis," *The Plant Cell* 6:75–83 (1994).

Wang et al., "The DEAH–Box Slicing Factor Prp 16 Unwinds RNA Duplexes in vitro," *Curr. Biol.* 8(8):441–451 (1998).

Levin et al., "UFO: An Arabidopsis Gene Involved in Both Floral Meristem and Floral Organ Development," *The Plant Cell* 7:529–548 (1995).

Walter et al., "Coaxial Stacking of Helixes Enhances Binding of Oligoribonucleotides and Improves Predictions of RNA Folding," *Proc. Natl. Acad. Sci. USA* 91(20):9218–9222 (1994).

Linder et al., "Birth of the D–E–A–D Box," *Nature* 337:121–122 (1989).

Lüking et al., "The Protein Family of RNA Helicases," *Critical Reviews in Biochemistry and Molecular Biology* 33(4):259–296 (1998).

Luo et al., "Genes Controlling Fertilization–Independent Seed Development in *Arabidopsis thaliana*," *Proc. Natl. Acd. Sci. USA* 96:296–301 (1999).

Cox et al., "Piwi Encodes a Nucleoplasmic Factor Whose Activity Modulates the Number and Division Rate of Germline Stem Cells," *Development* 127:503–514 (2000).

Ma, "The On and Off of Floral Regulatory Genes," *Cell* 89:821–824 (1997).

Macknight et al., "FCA, a Gene Controlling Flowering Time in Arabidopsis, Encodes a Protein Containing RNA–Binding Domains," *Cell* 89:737–745 (1997).

Mandel et al., "A Gene Triggering Flower Formation in Arabidopsis," *Nature* 377:522–524 (1995).

Mandel et al., "Molecular Characterization of the Arabidopsis Floral Homeotic Gene APETALA1," *Nature* 360:273–277 (1992).

Manseau et al., "Cappuccino and Spire: Two Unique Maternal–Effect Loci Required for Both the Anteroposterior and Dorsoventral Patterns of the Drosophila Embryo," *Genes and Development* 3:1437–1452 (1989).

Markussen et al., "Efficient Translation and Phosphorylation of Oskar Require Protein and the RNA Helicase Vasa," *Cold Spring Harb. Symp. Quant. Biol.* 62:13–17 (1997).

Martinez–Zapater et al., "The Transition to Flowering in Arabidopsis," In *Arabidopsis,* Meyerowitz et al., eds., Cold Spring Harbor Laboratory Press, Cold Spring Harbor, N.Y., pp. 403–433 (1994).

Torii et al., "The Arabidopsis ERECTA Gene Encodes a Putative Protein Kinase with Extracellular Leucine–Rich Repeats," *The Plant Cell* 8:735–746 (1996).

Suzuki et al., "The Conserved B3 Domain of VIVIPAROUS1 has a Cooperative DNA Binding Activity," *The Plant Cell* 9:799–807 (1997).

Tomancak et al., "Oocyte Polarity Depends n Regulation of Gurken by Vasa," *Development* 125:1723–1732 (1998).

Meinke, "Embryonic–Lethal Mutants of *Arabidopsis thaliana:* Analysis of Mutants with a Wide Range of Lethal Phases," *Theor. Appl. Genet.* 69:543–552 (1985).

Meinke, "Perspectives on Genetic Analysis of Plant Embryogenesis," *The Plant Cell* 3:857–866 (1991).

Mizukami et al., "Determination of Arabidopsis Floral Meristem Identity by AGAMOUS," *The Plant Cell* 9:393–408 (1997).

Modrusan et al., "Homeotic Transformation of Ovules into Carpel–like Structures in Arabidopsis," *The Plant Cell* 6:333–349 (1994).

Shevell et al., "EMB30 is Essential for Normal Cell Division, Cell Expansion, and Cell Adhesion in Arabidopsis and Encodes a Protein that has Similarity to SEc7," *Cell* 77:1051–1062 (1994).

Simon et al., "Activation of Floral Meristem Identity Genes in Arabidopsis," *Nature* 384:59–62 (1996).

Nüsslein–Volhard, "Genetic Analysis of Pattern–Formation in the Embryo of *Drosophila melanogaster:* Characterization of the Maternal–Effect Mutant Bicaudal," *Wilhelm Roux's Arch. Dev. Biol.* 183:249–268 (1977).

Ohad et al., "Mutations in FIE, a WD Polycomb Group Gene, Allow Endosperm Development Without Fertilization," *Plant Cell* 11:407–415 (1999).

Okamuro et al., "The AP2 Domain of APETALA2 Defines a large New Family of DNA Binding Proteins in Arabidopsis," *Proc. Natl. Acad. Sci. USA* 94:7076–7081 (1997).

Pause et al., "Mutational Analysis of a Dead Box RNA Helicase: The Mammalian Translation Initiation Factor eIF–4A," *EMBO J.* 11(7):2643–2654 (1992).

Shannon et al., "A Mutation in the Arabidopsis TTFL1 Gene Affects Inflorescence Meristem Development," *The Plant Cell* 3:877–892 (1991).

Shannon et al., "Genetic Interactions that Regulate Inflorescence Development in Arabidopsis," *The Plant Cell* 5:639–655 (1993).

Schwer et al., "Prp22, a DExH–Box RNA Helicase, Plays Two Distinct Roles in Yeast Pre–mRNA Splicing," *EMBO J.* 17(7):2086–2094 (1998).

Sengupta et al., "Identification of RNAs that Bind to a Specific Protein Using the Yeast Three–Hybrid System," *RNA* 5:596–601 (1999).

Putterill et al., "The CONSTANS Gene of Arabidopsis Promotes Flowering and Encodes a Protien Showing Similarities to Zinc Finger Transcription Factors," *Cell* 80:847–857 (1995).

Qu et al., "Seven Novel Methylation Guide Small Nucleolar RNAs are Processed from a Common Polycistronic Transcript by Rat1p and RNase III in Yeast," *Molecular and Cellular Biology* 19:1144–1158 (1999).

Ray et al., "Short INTEGUMENT (SINI), a Gene Required for Ovule Development in Arabidopsis, Also Controls Flowering Time,"0 *Development* 122:2631–2638 (1996).

Ray et al., "Arabidopsis Floral Homeotic Gene Bell (BEL1) Controls Ovule Development Through Negative Regulation of AGAMOUS Gene (AG)," *Proc. Natl. Acad. Sci. USA* 91:5761–5765 (1994).

Ray, "Three's Company: Regulatory Cross–Talk During Seed Development,"0 *The Plant Cell* 9:665–667 (1997).

Ray, "New Paradigms in Plant Embryogenesis: Maternal Control Comes in Different Flavors," *Trends in Plant Science* 3(9):325–327 (1998).

Ray et al., "Pollen Tube Guidance by the Female Gametophyte," *Development* 124:2489–2498 (1997).

Ray et al., "Maternal Effects of the Short Integument Mutation on Embryo Development in Arabidopsis," *Dev. Biol.* 180:365–369 (1996).

Reiser et al., "The Ovule and the Embryo Sac," *The Plant Cell* 5:1291–1301 (1993).

Reiser et al., "The BELL1 Gene Encodes a Homeodomain Protein Involved in Pattern Formation in the Arabidopsis Ovule Primordium," *Cell* 83:735–742 (1995).

Robinson–Beers et al., "Ovule Development in Wild–Type Arabidopsis and Two Female–Sterile Mutants," *The Plant Cell* 4:1237–1249 (1992).

Schultz et al., "Genetic Analysis of the Floral Initiation Process (FLIP) in Arabidopsis," *Development* 119:745–765 (1993).

Roush, "Probing Flowers' Genetic Past," *Science*:373:1339–1340 (1996).

Ryter et al., "Molecular Basis of Double–Stranded RNA–Protein Interactions: Structure of a dsRNA–Binding Domain Complexed with dsRNA," *EMBO J.* 17(24):7505–7513 (1998).

Sakai et al., "Role of Superman in Maintaining Arabidopsis Floral Whorl Boundaries," *Nature* 378:199–203 (1995).

Schena et al., "A Steroid–Inducible Gene Expression System for Plant Cells," *Proc. Natl. Acad. Sci. USA* 88:10421–10425 (1991).

Benfey, "Stem Cells: a Tale of Two Kingdoms," *Current Biology* 9(5):R171–R172 (1999).

Hunter, "Genetics: A Touch of Elegance with RNAi," *Current Biology* 9(12):R440–R442 (1999).

Hunter, "Gene Silencing: Shrinking the Black Box of RNAi," *Current Biology* 10(4):R137–R140 (2000).

Gasser et al., "Genetic Analysis of Ovule Development," *Annu. Rev. Plant Physiol. Plant Mol. Biol.* 49:1–24 (1998).

EMBL Database Accession No. AF187317 for *Arabidopsis thaliana* CAF Protein (CAF) mRNA, Complete CDS, Jacobsen et al., (1999).

EMBL Database Accession No. AF292940 for "The *Arabidopsis thanliana* Gene Short Integuments 1 (SINI) mRNA," Complete CDS, Golden et al. (2000).

* cited by examiner

SEQUENCE LISTING

<160> NUMBER OF SEQ ID NOS: 18

<210> SEQ ID NO 1
<211> LENGTH: 6184
<212> TYPE: DNA
<213> ORGANISM: Arabidopsis thaliana

<400> SEQUENCE: 1

```
gaagacgaag agagaaacag aacagagtag ggatcgatag accgtggaat ctcagaatca      60
caaacacttt gcaaagggt tttcaattcc tatttattta caaagaaatc atcaatagta      120
gtggtctcta gggttttgct tgctcttctt cgtgaccct ttttacctgc aaacaacaac      180
ttcaaaattg gcgtgtttcg tacggtctat ctaaccctaa tctgtcacaa aacactcttc      240
ttctctcacc cctttttctg ggtttattca attctcgtgc ttttggttct gttttcttct      300
```

-continued

```
ctggggattt ggttttcttg agtgagtttt tctcctcttt cttatgttct tgatttgatt    360
attatataga attatggtaa tggaggatga gcctagagaa gccacaataa agccttctta    420
ttggctagat gcttgcgagg acatctcttg tgatcttatc gatgatctcg tgtctgaatt    480
tgatccttcc tctgttgctg tcaatgaatc cactgatgaa aacggcgtca tcaatgattt    540
tttcggtggg attgatcaca ttttagatag tatcaagaac ggtggaggct taccaaacaa    600
tggcgtttct gataccaatt ctcaaatcaa cgaggttact gtaactcctc aggttattgc    660
taaggagaca gtgaaggaga atgggttgca aaagaatggc ggtaagagag acgaattctc    720
gaaagaggaa ggagacaagg ataggaagag agctagggtt tgtagttatc agagtgaaag    780
gagtaacctt tcaggtagag ggcatgttaa taattctagg gagggagata ggtttatgaa    840
taggaaacgt actcgtaatt gggacgaggc gggtaacaat aagaagaaaa gggaatgtaa    900
caattacaga agagatggta gagatagaga agttagggg tattgggaga gggataaagt     960
tggttccaat gagttggttt ataggtcagg gacttgggaa gctgatcatg aaagagatgt   1020
taagaaagtg agtggtggaa accgcgaatg cgatgtcaag gcagaggaga acaagagtaa   1080
gcctgaagaa cgtaaagaga aggttgtgga agagcaagca aggcgatacc agttggatgt   1140
tcttgaacaa gctaaagcga aaacacgat tgctttcctt gagaccggtg ctggaaagac    1200
acttatcgcg attcttctta ttaaaagtgt tcataaggat ctgatgagcc agaacagaaa   1260
aatgctctcg gtgttcttgg ttcccaaagt gcctttggtt tatcagcaag cagaagtgat   1320
ccgtaatcaa acttgttttc aagttggaca ttattgtggt gagatgggac aggacttttg   1380
ggattctcga aggtggcaac gagagtttga gtctaagcag gttctagtta tgacagcaca   1440
aattctgttg aatatactga gacacagtat cattagaatg gaaacaattg atcttcttat   1500
tctcgacgag tgtcaccacg ctgtcaagaa acatccatac tctttagtga tgtcagagtt   1560
ttaccataca actcctaaag ataaaagacc tgccatcttt ggaatgactg cttcgcctgt   1620
taatttaaag ggtgtttcaa gccaagtaga ttgtgcgata aagatacgta acctcgagac   1680
caagttggat tctacggttt gtactataaa agatcgaaaa gaattagaga acatgtgcc    1740 tatgccttca gagatagtcg tcgagtatga caaagctgct actatgtggt ctcttcatga   1800
gacaataaag caaatgattg cagctgttga agaagcggca caagcaagtt caaggaaaag   1860
caagtggcaa tttatgggg ctagggatgc tggagcaaag gatgaattga dacaggttta    1920
tggcgtctct gaaagaacgg agagcgatgg tgctgccaat ttgattcata aacttagagc   1980
tatcaattat actcttgctg aattgggtca atggtgtgct tacaaggtgg acaatcatt    2040 cttgtctgct ttgcaaagtg atgagagggt gaatttccaa gtcgacgtga agtttcaaga   2100
atcatacctc agtgaggtgg tgtcactctt gcaatgtgag cttctggaag gcgctgctgc   2160
tgaaaaagtc gcggcggaag ttggcaaacc agaaaatggt aatgcacatg acgagatgga   2220
ggagggagag ctccctgatg atcctgtggt ctcgggaggg gagcacgttg atgaagtaat   2280
aggcgccgca gtgctgatgg ggaaagttac tccaaaagta caatcattga tcaaactact   2340
cctcaaatat cagcacacag ctgattttcg agctattgtt ttcgttgaga gggtggttgc   2400
tgctttggtt cttcctaagg tttttgcgga gctgccttcg cttagttta tacggtgtgc    2460 cagcatgatt ggacacaata acagccagga gatgaaatca tctcaaatgc aggatacaat   2520
ttccaaattc cgagatgggc atgtgacact gttagtgcc acaagcgttg ctgaggaagg    2580
acttgatatt aggcaatgta acgttgttat gcgtttcgac cttgcaaaga cggtgctggc   2640
```

-continued

```
atacattcag tctcgtggcc gggcaagaaa gcctggatca gactacatac tcatggttga    2700
gagaggaaat gtatctcacg cagcgttcct aaggaatgct aggaacagtg aggagacact    2760
tcgaaaagaa gcaatagaaa ggactgatct tagtcatctc aaagatacat cgagattaat    2820
ctcaattgat gctgtgcctg gtacagttta aggtggag gcaactggtg ccatggttag      2880
cttgaattcc gcggttggtc ttgtacattt ctactgctct cagcttcctg gtgacaggta    2940
tgcaatcctt cgtcctgagt ttagcatgga gaagcatgaa aagcctgggg gccacacgga    3000
atattcatgt aggcttcagc ttccttgcaa tgcaccgttt gaaatacttg agggtcctgt    3060
ttgcagttca atgcgtcttg cacaacaggc tgtatgttta gctgcttgca agaaactgca    3120
tgagatgggt gcatttaccg atatgctatt accggacaaa ggaagtggtc aagacgctga    3180
gaaggctgac caagatgatg aaggtgagcc tgttcctgga actgctagac atagagagtt    3240
ctatcctgaa ggtgtggcgg atgtacttaa gggagaatgg gtttcatctg gaaggaagt     3300 ttgtgagagc tcaaagctat tccatttata catgtataat gtcagatgtg tagattttgg    3360
ctcttcaaaa gatccattcc taagcgaagt ttcagagttc gcgattcttt ttggcaatga    3420
gctggatgca gaggtattat cgatgtctat ggatctttat gttgctcggg ccatgatcac    3480
taaagcatct cttgctttca agggatcact tgatattaca gaaaaccagc tatcatctct    3540
aaaaaagttt catgtgaggt taatgagtat cgtgttggat gttgatgttg aaccctccac    3600
gacaccatgg gatcctgcaa aggcctacct gtttgtccct gttactgaca atacgtctat    3660
ggaacccata aaagggatca actgggaatt ggttgaaaag attacgaaaa ccacagcgtg    3720
ggacaaccct cttcagagag ctcgtcccga tgtatatctc gggactaatg agagaactct    3780
tggtggggac agaagggaat atgggtttgg taaacttcgt cacaacattg tatttgggca    3840
gaaatctcac ccaacttatg gtattagagg agctgttgca tccttcgatg ttgtgagagc    3900
ttctggattg ttacctgtga gagatgcttt tgagaaggaa gtagaagagg atttatcaaa    3960
aggaaaattg atgatggctg atgggtgcat ggttgcagaa gatcttattg ggaaaatagt    4020
gacagccgca cattccggga agcggtttta cgtagattca atttgttatg catgagtgc     4080 agaaacatct ttccctagga aagagggata tcttggtccc ctagagtaca acacgtacgc    4140
tgactattac aagcaaaagt atggagttga tttgaactgt aagcaacaac ctttgattaa    4200
aggacgtggt gtttcgtatt gcaagaacct tctttctcct cggtttgaac agtcaggtga    4260
atctgagaca gtccttgata agacatatta cgtgtttctt ccacctgaac tatgcgttgt    4320
gcatccgctt tcgggttcac ttatccgagg tgctcagagg ttaccctcta taatgagaag    4380
agttgagagc atgttactcg ctgttcaact caaaaatttg attagttatc ctattcccac    4440
atcaaagatt cttgaagcct tgactgccgc ctcgtgccag gaaacgttct gctacgagag    4500
agctgagctt ttaggagatg cgtatctaaa atgggttgtt agtcgttttc tgtttctcaa    4560
gtatcctcaa aagcacgagg gtcagcttac aaggatgagg caacaaatgg ttagtaatat    4620
ggttctttat cagtttgctc tggttaaagg gcttcagtca tatatccagg cggatcgatt    4680
cgccccgtct aggtggtctg ctcctggtgt gcctccggtt ttcgacgagg acacaaaaga    4740
tggaggatct tcgttttttcg atgaagagca aaaacctgtt tccgaggaaa acagcgatgt    4800
gtttgaagat ggggagatgg aggatggtga actagagggt gatttgagtt cgtaccgagt    4860
tttatctagc aaaacgttag ctgatgttgt tgaggctttg attggtgttt attacgtcga    4920 aggggggtaag attgcagcta atcatttgat gaaatggatt gggattcacg tggaggatga    4980
tcctgatgaa gtcgatggaa cattgaaaaa tgttaatgtt ccagagagtg tgctcaagag    5040
```

```
catcgacttt gttggtcttg agagagctct taaatatgag tttaaagaga aaggtcttct   5100
tgttgaagct ataacacatg cttcaagacc atcttcaggt gtttcgtgtt accagagatt   5160
ggaatttgtt ggtgacgcgg tcttggatca tctcatcaca agacatctat ttttcacata   5220
cacaagcctt cctcctggtc ggttaacaga tcttcgagct gcagcggtta acaacgagaa   5280
ttttgctcgc gttgcggtta aacataaact ccacttgtac cttcgtcacg gttcaagcgc   5340
cctcgaaaaa cagattcggg aatttgtgaa ggaggttcaa accgagtcat cgaaaccggg   5400
gtttaactct tttggtttgg gagactgcaa agcaccaaaa gttcttggag acattgttga   5460
atctattgca ggtgctattt ttcttgatag tggaaaagat acaactgctg cttggaaggt   5520
ttttcaacct ttgcttcagc ccatggtgac accagagaca cttccaatgc atccggtgcg   5580
agagctacaa gagcggtgcc agcaacaagc agaagggtta gaatacaaag cgagtaggag   5640
tggtaacaca gcgactgtgg aagttttcat cgacggtgtt caagttggag tagcgcaaaa   5700
cccgcagaag aaaatggctc aaaagctagc tgcgaggaac gcacttgcag ctttgaaaga   5760
gaaagaaata gcagaatcaa aggagaagca tatcaacaac ggtaatgcgg gagaggatca   5820
aggcgagaat gagaatggga acaagaagaa tgggcatcag ccgtttacga gacaaacgtt   5880
gaatgatatt tgtttgagga agaattggcc aatgccttct tacagatgtg tgaaagaagg   5940
aggaccggct catgcaaaga gatttacgtt tggggtaaga gttaatacga gcgatagagg   6000
atggaccgat gagtgtattg gcgagccaat gccgagtgtt aagaaagcta aggattcagc   6060
tgcggttctt ctacttgagc ttttaaataa aacttttcct tgattctttt actctcttca   6120
acgagatgta gtcattacat tttaaacctt aaaaccatag tggttgtagt gttttaaaaa   6180
aaaa                                                               6184

<210> SEQ ID NO 2
<211> LENGTH: 1909
<212> TYPE: PRT
<213> ORGANISM: Arabidopsis thaliana

<400> SEQUENCE: 2

Met Val Met Glu Asp Glu Pro Arg Glu Ala Thr Ile Lys Pro Ser Tyr
  1               5                  10                  15

Trp Leu Asp Ala Cys Glu Asp Ile Ser Cys Asp Leu Ile Asp Asp Leu
                 20                  25                  30

Val Ser Glu Phe Asp Pro Ser Ser Val Ala Val Asn Glu Ser Thr Asp
             35                  40                  45

Glu Asn Gly Val Ile Asn Asp Phe Phe Gly Gly Ile Asp His Ile Leu
         50                  55                  60

Asp Ser Ile Lys Asn Gly Gly Gly Leu Pro Asn Asn Gly Val Ser Asp
 65                  70                  75                  80

Thr Asn Ser Gln Ile Asn Glu Val Thr Val Thr Pro Gln Val Ile Ala
                 85                  90                  95

Lys Glu Thr Val Lys Glu Asn Gly Leu Gln Lys Asn Gly Gly Lys Arg
            100                 105                 110

Asp Glu Phe Ser Lys Glu Glu Gly Asp Lys Asp Arg Lys Arg Ala Arg
        115                 120                 125

Val Cys Ser Tyr Gln Ser Glu Arg Ser Asn Leu Ser Gly Arg Gly His
    130                 135                 140

Val Asn Asn Ser Arg Glu Gly Asp Arg Phe Met Asn Arg Lys Arg Thr
145                 150                 155                 160
```

-continued

```
Arg Asn Trp Asp Glu Ala Gly Asn Asn Lys Lys Arg Glu Cys Asn
                165                 170                 175

Asn Tyr Arg Arg Asp Gly Arg Asp Arg Glu Val Arg Gly Tyr Trp Glu
        180                 185                 190

Arg Asp Lys Val Gly Ser Asn Glu Leu Val Tyr Arg Ser Gly Thr Trp
            195                 200                 205

Glu Ala Asp His Glu Arg Asp Val Lys Lys Val Ser Gly Gly Asn Arg
        210                 215                 220

Glu Cys Asp Val Lys Ala Glu Glu Asn Lys Ser Lys Pro Glu Glu Arg
225                 230                 235                 240

Lys Glu Lys Val Val Glu Glu Gln Ala Arg Arg Tyr Gln Leu Asp Val
                245                 250                 255

Leu Glu Gln Ala Lys Ala Lys Asn Thr Ile Ala Phe Leu Glu Thr Gly
            260                 265                 270

Ala Gly Lys Thr Leu Ile Ala Ile Leu Leu Ile Lys Ser Val His Lys
        275                 280                 285

Asp Leu Met Ser Gln Asn Arg Lys Met Leu Ser Val Phe Leu Val Pro
    290                 295                 300

Lys Val Pro Leu Val Tyr Gln Gln Ala Glu Val Ile Arg Asn Gln Thr
305                 310                 315                 320

Cys Phe Gln Val Gly His Tyr Cys Gly Glu Met Gly Gln Asp Phe Trp
                325                 330                 335

Asp Ser Arg Arg Trp Gln Arg Glu Phe Glu Ser Lys Gln Val Leu Val
            340                 345                 350

Met Thr Ala Gln Ile Leu Leu Asn Ile Leu Arg His Ser Ile Ile Arg
        355                 360                 365

Met Glu Thr Ile Asp Leu Leu Ile Leu Asp Glu Cys His His Ala Val
    370                 375                 380

Lys Lys His Pro Tyr Ser Leu Val Met Ser Glu Phe Tyr His Thr Thr
385                 390                 395                 400

Pro Lys Asp Lys Arg Pro Ala Ile Phe Gly Met Thr Ala Ser Pro Val
                405                 410                 415

Asn Leu Lys Gly Val Ser Ser Gln Val Asp Cys Ala Ile Lys Ile Arg
            420                 425                 430

Asn Leu Glu Thr Lys Leu Asp Ser Thr Val Cys Thr Ile Lys Asp Arg
        435                 440                 445

Lys Glu Leu Glu Lys His Val Pro Met Pro Ser Glu Ile Val Val Glu
    450                 455                 460

Tyr Asp Lys Ala Ala Thr Met Trp Ser Leu His Glu Thr Ile Lys Gln
465                 470                 475                 480

Met Ile Ala Ala Val Glu Glu Ala Ala Gln Ala Ser Ser Arg Lys Ser
                485                 490                 495

Lys Trp Gln Phe Met Gly Ala Arg Asp Ala Gly Ala Lys Asp Glu Leu
            500                 505                 510

Arg Gln Val Tyr Gly Val Ser Glu Arg Thr Glu Ser Asp Gly Ala Ala
        515                 520                 525

Asn Leu Ile His Lys Leu Arg Ala Ile Asn Tyr Thr Leu Ala Glu Leu
    530                 535                 540

Gly Gln Trp Cys Ala Tyr Lys Val Gly Gln Ser Phe Leu Ser Ala Leu
545                 550                 555                 560

Gln Ser Asp Glu Arg Val Asn Phe Gln Val Asp Val Lys Phe Gln Glu
                565                 570                 575

Ser Tyr Leu Ser Glu Val Val Ser Leu Leu Gln Cys Glu Leu Leu Glu
```

-continued

```
                  580                     585                     590
Gly Ala Ala Ala Glu Lys Val Ala Glu Val Gly Lys Pro Glu Asn
            595                     600                     605
Gly Asn Ala His Asp Glu Met Glu Glu Gly Leu Pro Asp Asp Pro
610                     615                     620
Val Val Ser Gly Gly Glu His Val Asp Glu Val Ile Gly Ala Val
625                     630                     635                     640
Ala Asp Gly Lys Val Thr Pro Lys Val Gln Ser Leu Ile Lys Leu Leu
            645                     650                     655
Leu Lys Tyr Gln His Thr Ala Asp Phe Arg Ala Ile Val Phe Val Glu
            660                     665                     670
Arg Val Val Ala Ala Leu Val Leu Pro Lys Val Phe Ala Glu Leu Pro
            675                     680                     685
Ser Leu Ser Phe Ile Arg Cys Ala Ser Met Ile Gly His Asn Asn Ser
            690                     695                     700
Gln Glu Met Lys Ser Ser Gln Met Gln Asp Thr Ile Ser Lys Phe Arg
705                     710                     715                     720
Asp Gly His Val Thr Leu Leu Val Ala Thr Ser Val Ala Glu Glu Gly
            725                     730                     735
Leu Asp Ile Arg Gln Cys Asn Val Val Met Arg Phe Asp Leu Ala Lys
            740                     745                     750
Thr Val Leu Ala Tyr Ile Gln Ser Arg Gly Arg Ala Arg Lys Pro Gly
            755                     760                     765
Ser Asp Tyr Ile Leu Met Val Glu Arg Gly Asn Val Ser His Ala Ala
770                     775                     780
Phe Leu Arg Asn Ala Arg Asn Ser Glu Glu Thr Leu Arg Lys Glu Ala
785                     790                     795                     800
Ile Glu Arg Thr Asp Leu Ser His Leu Lys Asp Thr Ser Arg Leu Ile
            805                     810                     815
Ser Ile Asp Ala Val Pro Gly Thr Val Tyr Lys Val Glu Ala Thr Gly
            820                     825                     830
Ala Met Val Ser Leu Asn Ser Ala Val Gly Leu Val His Phe Tyr Cys
            835                     840                     845
Ser Gln Leu Pro Gly Asp Arg Tyr Ala Ile Leu Arg Pro Glu Phe Ser
850                     855                     860
Met Glu Lys His Glu Lys Pro Gly Gly His Thr Glu Tyr Ser Cys Arg
865                     870                     875                     880
Leu Gln Leu Pro Cys Asn Ala Pro Phe Glu Ile Leu Glu Gly Pro Val
            885                     890                     895
Cys Ser Ser Met Arg Leu Ala Gln Gln Ala Val Cys Leu Ala Ala Cys
            900                     905                     910
Lys Lys Leu His Glu Met Gly Ala Phe Thr Asp Met Leu Leu Pro Asp
            915                     920                     925
Lys Gly Ser Gly Gln Asp Ala Glu Lys Ala Asp Gln Asp Asp Glu Gly
930                     935                     940
Glu Pro Val Pro Gly Thr Ala Arg His Arg Glu Phe Tyr Pro Glu Gly
945                     950                     955                     960
Val Ala Asp Val Leu Lys Gly Glu Trp Val Ser Ser Gly Lys Glu Val
            965                     970                     975
Cys Glu Ser Ser Lys Leu Phe His Leu Tyr Met Tyr Asn Val Arg Cys
            980                     985                     990
Val Asp Phe Gly Ser Ser Lys Asp Pro Phe Leu Ser Glu Val Ser Glu
            995                     1000                    1005
```

```
Phe Ala Ile Leu Phe Gly Asn Glu Leu Asp Ala Glu Val Leu Ser Met
    1010                1015                1020

Ser Met Asp Leu Tyr Val Ala Arg Ala Met Ile Thr Lys Ala Ser Leu
1025                1030                1035                1040

Ala Phe Lys Gly Ser Leu Asp Ile Thr Glu Asn Gln Leu Ser Ser Leu
            1045                1050                1055

Lys Lys Phe His Val Arg Leu Met Ser Ile Val Leu Asp Val Asp Val
            1060                1065                1070

Glu Pro Ser Thr Thr Pro Trp Asp Pro Ala Lys Ala Tyr Leu Phe Val
        1075                1080                1085

Pro Val Thr Asp Asn Thr Ser Met Glu Pro Ile Lys Gly Ile Asn Trp
    1090                1095                1100

Glu Leu Val Glu Lys Ile Thr Lys Thr Thr Ala Trp Asp Asn Pro Leu
1105                1110                1115                1120

Gln Arg Ala Arg Pro Asp Val Tyr Leu Gly Thr Asn Glu Arg Thr Leu
            1125                1130                1135

Gly Gly Asp Arg Arg Glu Tyr Gly Phe Gly Lys Leu Arg His Asn Ile
            1140                1145                1150

Val Phe Gly Gln Lys Ser His Pro Thr Tyr Gly Ile Arg Gly Ala Val
        1155                1160                1165

Ala Ser Phe Asp Val Val Arg Ala Ser Gly Leu Leu Pro Val Arg Asp
1170                1175                1180

Ala Phe Glu Lys Glu Val Glu Glu Asp Leu Ser Lys Gly Lys Leu Met
1185                1190                1195                1200

Met Ala Asp Gly Cys Met Val Ala Glu Asp Leu Ile Gly Lys Ile Val
            1205                1210                1215

Thr Ala Ala His Ser Gly Lys Arg Phe Tyr Val Asp Ser Ile Cys Tyr
            1220                1225                1230

Asp Met Ser Ala Glu Thr Ser Phe Pro Arg Lys Glu Gly Tyr Leu Gly
            1235                1240                1245

Pro Leu Glu Tyr Asn Thr Tyr Ala Asp Tyr Tyr Lys Gln Lys Tyr Gly
    1250                1255                1260

Val Asp Leu Asn Cys Lys Gln Gln Pro Leu Ile Lys Gly Arg Gly Val
1265                1270                1275                1280

Ser Tyr Cys Lys Asn Leu Leu Ser Pro Arg Phe Glu Gln Ser Gly Glu
            1285                1290                1295

Ser Glu Thr Val Leu Asp Lys Thr Tyr Tyr Val Phe Leu Pro Pro Glu
            1300                1305                1310

Leu Cys Val Val His Pro Leu Ser Gly Ser Leu Ile Arg Gly Ala Gln
    1315                1320                1325

Arg Leu Pro Ser Ile Met Arg Arg Val Glu Ser Met Leu Leu Ala Val
    1330                1335                1340

Gln Leu Lys Asn Leu Ile Ser Tyr Pro Ile Pro Thr Ser Lys Ile Leu
1345                1350                1355                1360

Glu Ala Leu Thr Ala Ala Ser Cys Gln Glu Thr Phe Cys Tyr Glu Arg
            1365                1370                1375

Ala Glu Leu Leu Gly Asp Ala Tyr Leu Lys Trp Val Val Ser Arg Phe
            1380                1385                1390

Leu Phe Leu Lys Tyr Pro Gln Lys His Glu Gly Gln Leu Thr Arg Met
        1395                1400                1405

Arg Gln Gln Met Val Ser Asn Met Val Leu Tyr Gln Phe Ala Leu Val
    1410                1415                1420
```

```
Lys Gly Leu Gln Ser Tyr Ile Gln Ala Asp Arg Phe Ala Pro Ser Arg
1425                1430                1435                1440

Trp Ser Ala Pro Gly Val Pro Pro Val Phe Asp Glu Asp Thr Lys Asp
            1445                1450                1455

Gly Gly Ser Ser Phe Phe Asp Glu Glu Gln Lys Pro Val Ser Glu Glu
        1460                1465                1470

Asn Ser Asp Val Phe Glu Asp Gly Glu Met Glu Asp Gly Glu Leu Glu
    1475                1480                1485

Gly Asp Leu Ser Ser Tyr Arg Val Leu Ser Ser Lys Thr Leu Ala Asp
1490                1495                1500

Val Val Glu Ala Leu Ile Gly Val Tyr Val Glu Gly Gly Lys Ile
1505                1510                1515                1520

Ala Ala Asn His Leu Met Lys Trp Ile Gly Ile His Val Glu Asp Asp
            1525                1530                1535

Pro Asp Glu Val Asp Gly Thr Leu Lys Asn Val Asn Val Pro Glu Ser
        1540                1545                1550

Val Leu Lys Ser Ile Asp Phe Val Gly Leu Glu Arg Ala Leu Lys Tyr
    1555                1560                1565

Glu Phe Lys Glu Lys Gly Leu Leu Val Glu Ala Ile Thr His Ala Ser
1570                1575                1580

Arg Pro Ser Ser Gly Val Ser Cys Tyr Gln Arg Leu Glu Phe Val Gly
1585                1590                1595                1600

Asp Ala Val Leu Asp His Leu Ile Thr Arg His Leu Phe Phe Thr Tyr
            1605                1610                1615

Thr Ser Leu Pro Pro Gly Arg Leu Thr Asp Leu Arg Ala Ala Ala Val
        1620                1625                1630

Asn Asn Glu Asn Phe Ala Arg Val Ala Val Lys His Lys Leu His Leu
    1635                1640                1645

Tyr Leu Arg His Gly Ser Ser Ala Leu Glu Lys Gln Ile Arg Glu Phe
1650                1655                1660

Val Lys Glu Val Gln Thr Glu Ser Ser Lys Pro Gly Phe Asn Ser Phe
1665                1670                1675                1680

Gly Leu Gly Asp Cys Lys Ala Pro Lys Val Leu Gly Asp Ile Val Glu
            1685                1690                1695

Ser Ile Ala Gly Ala Ile Phe Leu Asp Ser Gly Lys Asp Thr Thr Ala
        1700                1705                1710

Ala Trp Lys Val Phe Gln Pro Leu Leu Gln Pro Met Val Thr Pro Glu
    1715                1720                1725

Thr Leu Pro Met His Pro Val Arg Glu Leu Gln Glu Arg Cys Gln Gln
1730                1735                1740

Gln Ala Glu Gly Leu Glu Tyr Lys Ala Ser Arg Ser Gly Asn Thr Ala
1745                1750                1755                1760

Thr Val Glu Val Phe Ile Asp Gly Val Gln Val Gly Val Ala Gln Asn
            1765                1770                1775

Pro Gln Lys Lys Met Ala Gln Lys Leu Ala Ala Arg Asn Ala Leu Ala
        1780                1785                1790

Ala Leu Lys Glu Lys Glu Ile Ala Glu Ser Lys Glu Lys His Ile Asn
    1795                1800                1805

Asn Gly Asn Ala Gly Glu Asp Gln Gly Glu Asn Glu Asn Gly Asn Lys
1810                1815                1820

Lys Asn Gly His Gln Pro Phe Thr Arg Gln Thr Leu Asn Asp Ile Cys
1825                1830                1835                1840

Leu Arg Lys Asn Trp Pro Met Pro Ser Tyr Arg Cys Val Lys Glu Gly
```

```
                    1845              1850              1855
Gly Pro Ala His Ala Lys Arg Phe Thr Phe Gly Val Arg Val Asn Thr
            1860              1865              1870

Ser Asp Arg Gly Trp Thr Asp Glu Cys Ile Gly Glu Pro Met Pro Ser
        1875              1880              1885

Val Lys Lys Ala Lys Asp Ser Ala Ala Val Leu Leu Leu Glu Leu Leu
    1890              1895              1900

Asn Lys Thr Phe Ser
1905

<210> SEQ ID NO 3
<211> LENGTH: 79
<212> TYPE: PRT
<213> ORGANISM: Drosophila

<400> SEQUENCE: 3

Asp Phe Leu Ala Ser Phe Leu Ser Glu Lys Thr Thr Ser Ile His Gly
  1               5                  10                  15

Asp Arg Leu Gln Ser Gln Arg Glu Gln Ala Leu Arg Asp Phe Lys Asn
             20                  25                  30

Gly Ser Met Lys Val Leu Ile Ala Thr Ser Val Ala Ser Arg Gly Leu
         35                  40                  45

Asp Ile Lys Asn Ile Lys His Val Ile Asn Tyr Asp Met Pro Ser Lys
     50                  55                  60

Ile Asp Asp Tyr Val His Arg Ile Gly Arg Thr Gly Cys Val Gly
 65                  70                  75

<210> SEQ ID NO 4
<211> LENGTH: 78
<212> TYPE: PRT
<213> ORGANISM: S. cerevisae

<400> SEQUENCE: 4

His Arg Leu Arg Ile Ile Met Gly Leu Leu Val Gly Glu Leu His Gly
  1               5                  10                  15

Ser Leu Thr Gln Glu Gln Arg Leu Asp Ser Val Asn Lys Phe Lys Asn
             20                  25                  30

Leu Glu Val Pro Val Leu Ile Cys Thr Asp Leu Ala Ser Arg Gly Leu
         35                  40                  45

Asp Ile Pro Lys Ile Glu Val Val Ile Asn Tyr Asp Met Pro Lys Ser
     50                  55                  60

Tyr Glu Ile Tyr Leu His Arg Val Gly Arg Thr Ala Arg Ala
 65                  70                  75

<210> SEQ ID NO 5
<211> LENGTH: 78
<212> TYPE: PRT
<213> ORGANISM: Arabidopsis thaliana

<400> SEQUENCE: 5

Leu Val Leu Pro Lys Val Phe Ala Glu Leu Ser Met Ile Gly His Asn
  1               5                  10                  15

Glu Met Lys Ser Ser Gln Met Gln Asp Thr Ile Ser Lys Phe Arg Asp
             20                  25                  30

Gly His Val Thr Leu Leu Val Ala Thr Ser Val Ala Glu Glu Gly Leu
         35                  40                  45

Asp Ile Arg Gln Cys Asn Val Val Met Arg Phe Asp Leu Ala Lys Thr
     50                  55                  60
```

```
Val Leu Ala Tyr Ile Gln Ser Arg Gly Arg Ala Arg Lys Pro
 65                  70                  75
```

<210> SEQ ID NO 6
<211> LENGTH: 82
<212> TYPE: PRT
<213> ORGANISM: S. cerevisae

<400> SEQUENCE: 6

```
Glu Arg Leu Ser Gly Leu Cys Asn Leu Leu Glu Phe Ser Ala Thr Ala
  1               5                  10                  15

Leu His Gly Asp Leu Asn Gln Asn Gln Arg Met Gly Ser Leu Asp Leu
             20                  25                  30

Phe Lys Ala Gly Lys Arg Ser Ile Leu Val Ala Thr Asp Val Ala Ala
         35                  40                  45

Arg Gly Leu Asp Ile Pro Ser Val Asp Ile Val Asn Tyr Asp Ile
     50                  55                  60

Pro Val Asp Ser Lys Ser Tyr Ile His Arg Val Gly Arg Thr Ala Arg
 65                  70                  75                  80

Ala Gly
```

<210> SEQ ID NO 7
<211> LENGTH: 81
<212> TYPE: PRT
<213> ORGANISM: S. cerevisae

<400> SEQUENCE: 7

```
His Arg Leu Arg Ile Ile Met Gly Leu Leu Gly Met Ser Val Gly Glu
  1               5                  10                  15

Leu His Gly Ser Leu Thr Gln Glu Gln Arg Leu Asp Ser Val Asn Lys
             20                  25                  30

Phe Lys Asn Leu Glu Val Pro Val Leu Ile Cys Thr Asp Leu Ala Ser
         35                  40                  45

Arg Gly Leu Asp Ile Pro Lys Ile Glu Val Val Ile Asn Tyr Asp Met
     50                  55                  60

Pro Lys Ser Tyr Glu Ile Leu His Arg Val Gly Arg Thr Ala Arg Ala
 65                  70                  75                  80

Gly
```

<210> SEQ ID NO 8
<211> LENGTH: 82
<212> TYPE: PRT
<213> ORGANISM: Drosophila

<400> SEQUENCE: 8

```
Asp Phe Leu Ala Ser Phe Leu Ser Glu Lys Glu Phe Pro Thr Thr Ser
  1               5                  10                  15

Ile His Gly Asp Arg Leu Gln Ser Gln Arg Glu Gln Ala Leu Arg Asp
             20                  25                  30

Phe Lys Asn Gly Ser Met Lys Val Leu Ile Ala Thr Ser Val Ala Ser
         35                  40                  45

Arg Gly Leu Asp Ile Lys Asn Ile Lys His Val Ile Asn Tyr Asp Met
     50                  55                  60

Pro Ser Lys Ile Asp Asp Tyr Val His Arg Ile Gly Arg Thr Gly Cys
 65                  70                  75                  80

Val Gly
```

```
<210> SEQ ID NO 9
<211> LENGTH: 81
<212> TYPE: PRT
<213> ORGANISM: Arabidopsis thaliana

<400> SEQUENCE: 9

Lys Val Phe Ala Glu Leu Pro Ser Leu Ser Phe Ile Arg Cys Ala Ser
 1               5                  10                  15

Met Ile Gly Glu Met Lys Ser Ser Gln Met Gln Asp Thr Ile Ser Lys
            20                  25                  30

Phe Arg Asp Gly His Val Thr Leu Leu Val Ala Thr Ser Val Ala Glu
        35                  40                  45

Glu Gly Leu Asp Ile Arg Gln Cys Asn Val Val Met Arg Phe Asp Leu
    50                  55                  60

Ala Lys Thr Val Leu Ala Tyr Ile Gln Ser Arg Gly Arg Ala Arg Lys
65                  70                  75                  80

Pro

<210> SEQ ID NO 10
<211> LENGTH: 41
<212> TYPE: PRT
<213> ORGANISM: S. pombe

<400> SEQUENCE: 10

Glu Arg Leu Glu Phe Leu Gly Asp Ser Phe Asn Leu Phe Thr Thr
 1               5                  10                  15

Arg Ile Ile Phe Ser Lys Phe Pro Gln Met Asp Glu Gly Ser Leu Ser
            20                  25                  30

Lys Leu Arg Arg Lys Phe Val Gly Asn
        35                  40

<210> SEQ ID NO 11
<211> LENGTH: 41
<212> TYPE: PRT
<213> ORGANISM: Drosophila

<400> SEQUENCE: 11

Glu Arg Leu Glu Phe Leu Gly Asp Ser Val Leu Gly Phe Ile Ile Ala
 1               5                  10                  15

Ser Glu Leu Tyr Gln Arg Arg Pro Gln Ala Arg Glu Gly Asp Leu Ser
            20                  25                  30

Arg Met Arg Ala Ser Met Val Asn Gly
        35                  40

<210> SEQ ID NO 12
<211> LENGTH: 41
<212> TYPE: PRT
<213> ORGANISM: C. elegans

<400> SEQUENCE: 12

Gln Arg Leu Glu Phe Leu Gly Asp Ala Val Leu Asp Tyr Met Ile Thr
 1               5                  10                  15

Arg Tyr Leu Phe Glu Asp Ser Arg Gln Tyr Ser Pro Gly Val Leu Thr
            20                  25                  30

Asp Leu Arg Ser Ala Leu Val Asn Asn
        35                  40

<210> SEQ ID NO 13
<211> LENGTH: 41
```

```
<212> TYPE: PRT
<213> ORGANISM: Arabidopsis thaliana

<400> SEQUENCE: 13

Glu Arg Ala Glu Leu Leu Gly Asp Ala Tyr Leu Lys Trp Val Val Ser
 1               5                  10                  15

Arg Phe Leu Phe Leu Lys Tyr Pro Gln Lys His Glu Gly Gln Leu Thr
                20                  25                  30

Arg Met Arg Gln Gln Met Val Ser Asn
        35                  40

<210> SEQ ID NO 14
<211> LENGTH: 65
<212> TYPE: PRT
<213> ORGANISM: Drosophila

<400> SEQUENCE: 14

Pro Met Cys Leu Val Asn Glu Leu Ala Arg Tyr Asn Lys Ile Thr His
 1               5                  10                  15

Gln Tyr Arg Leu Thr Glu Glu Arg Gly Pro Ala His Cys Lys Thr Phe
                20                  25                  30

Thr Val Thr Leu Met Leu Gly Asp Glu Glu Tyr Ser Ala Asp Gly Phe
        35                  40                  45

Lys Ile Lys Lys Ala Gln His Leu Ala Ala Ser Lys Ala Ile Glu Glu
    50                  55                  60

Thr
 65

<210> SEQ ID NO 15
<211> LENGTH: 65
<212> TYPE: PRT
<213> ORGANISM: Drosophila

<400> SEQUENCE: 15

Pro Ile Ser Gln Val His Glu Ile Gly Ile Lys Arg Asn Met Thr Val
 1               5                  10                  15

His Phe Lys Val Leu Arg Glu Glu Gly Pro Ala His Met Lys Asn Phe
                20                  25                  30

Ile Thr Ala Cys Ile Val Gly Ser Ile Val Thr Glu Gly Glu Gly Asn
        35                  40                  45

Gly Lys Lys Val Ser Lys Arg Ala Ala Glu Lys Met Leu Val Glu
    50                  55                  60

Leu
 65

<210> SEQ ID NO 16
<211> LENGTH: 64
<212> TYPE: PRT
<213> ORGANISM: Drosophila

<400> SEQUENCE: 16

Pro Ile Thr Lys Leu Ile Gln Leu Gln Gln Thr Arg Lys Glu Lys Glu
 1               5                  10                  15

Pro Ile Phe Glu Leu Ile Ala Asn Gly Asn Glu Thr Ala Arg Arg Arg
                20                  25                  30

Phe Val Met Glu Val Ser Ala Ser Gly Ser Thr Ala Arg Gly Thr Gly
        35                  40                  45

Asn Ser Lys Leu Ala Lys Arg Asn Ala Ala Gln Ala Leu Phe Glu Leu
    50                  55                  60
```

```
<210> SEQ ID NO 17
<211> LENGTH: 73
<212> TYPE: PRT
<213> ORGANISM: Arabidopsis thaliana

<400> SEQUENCE: 17

Thr Arg Gln Thr Leu Asn Asp Ile Cys Leu Arg Lys Asn Trp Pro Met
  1               5                  10                  15

Pro Ser Tyr Arg Cys Val Lys Glu Gly Gly Pro Ala His Ala Lys Arg
             20                  25                  30

Phe Thr Phe Gly Val Arg Val Asn Thr Ser Asp Arg Gly Trp Thr Asp
         35                  40                  45

Glu Cys Ile Gly Glu Pro Met Pro Ser Val Lys Lys Ala Lys Asp Ser
     50                  55                  60

Ala Ala Val Leu Leu Leu Glu Leu Leu
 65                  70

<210> SEQ ID NO 18
<211> LENGTH: 61
<212> TYPE: PRT
<213> ORGANISM: Arabidopsis thaliana

<400> SEQUENCE: 18

Pro Val Arg Glu Leu Gln Glu Arg Cys Gln Gln Gln Ala Glu Gly Leu
  1               5                  10                  15

Glu Tyr Lys Ala Ser Arg Ser Gly Asn Thr Ala Thr Val Glu Val Phe
             20                  25                  30

Ile Asp Gly Val Gln Val Gly Val Ala Gln Asn Pro Gln Lys Lys Met
         35                  40                  45

Ala Gln Lys Leu Ala Ala Arg Asn Ala Leu Ala Leu
     50                  55                  60
```

US 6,737,561 B1

GENE ENCODING SHORT INTEGUMENTS AND USES THEREOF

This application claims the benefit of U.S. Provisional Patent Application Serial No. 60/138,316, filed Jun. 9, 1999.

This invention was developed with government funding by the National Science Foundation, Grant No. IBN-9728239. The U.S. Government may have certain rights.

FIELD OF THE INVENTION

The invention relates to short integuments1 nucleic acids and proteins, and to plants having altered phenotypes when transformed with short integumentsl nucleic acids.

BACKGROUND OF THE INVENTION

According to recent estimates, the global demand for crop plants such as rice, wheat, and maize should increase by 40% by 2020. It is thought that classical plant breeding technology, which led to the green revolution in the late 1960s, will contribute less and less to meet this increasing demand, whereas plant genetic engineering will contribute increasingly more. An important thrust area in plant genetic engineering is the identification and use of genes implicated in asexual production of seeds, or "apomixis." Apomixis is thought to be an agronomically desirable trait that should enable seed companies and farmers to lock-in a favorable combination of genes for maximum grain yield without having to lose the gene combination in the next sexual generation. Genes for apomixis have not yet been identified. It is thought that genes that are generally important for very early embryo/seed development may be important for apomixis. A second important thrust is the production of early flowering varieties of plants such that breeding time can be reduced.

The evolution of flowering plants may have entailed a modification of primitive leaf or leaf-like structures that contained naked ovules on their surfaces, to specify floral organs that ultimately evolved to surround the ovules (Herr, "The Origin of the Ovule," Am. J. Bot. 82:547–564 (1995); Stebbins, Flowering Plants: Evolution Above the Species Level, Cambridge, Mass.: Harvard University Press, pp. 199–245). This view of angiosperm evolution predicts that the genetic regulatory network that controls ovule development should be interlaced with that which triggers flowering. Ovule, as the precursor of seed, is the link to the next generation. Genetic regulatory pathways that are important for early vegetative development of the embryo inside the ovule, for late reproductive development leading to the production of ovules, and for morphogenesis of the haploid female gametophyte, are crucial areas of investigation which can lead to enhanced agricultural practices.

Several genes important for ovule development have been identified in Arabidopsis thaliana (Reiser et al., "The Ovule and the Embryo Sac," The Plant Cell 5:1291–1301 (1993)). BELL1, a so-called cadastral gene that encodes a homeodomain protein (Reiser et al., "The BELL1 Gene Encodes a Homeodomain Protein Involved in Pattern Formation in the Arabidopsis Ovule Primordium," Cell 83, 735–742 (1995)), controls the expression of the floral organ identity gene AG within the ovule and thereby controls morphogenesis of ovule integuments (Modrusan et al., "Homeotic Transformation of Ovules into Carpel-Like Structures in Arabidopsis," The Plant Cell 6:333–349 (1994); Ray et al., "The Arabidopsis Floral Homeotic Gene BELL (BEL1) Controls Ovule Development Through Negative Regulation of AGAMOUS (AG) Gene," Proc. Natl. Acad. Sci. USA 91:5761–5765 (1994)). SUPERMAN, another cadastral gene that restricts the spatial expression pattern of the floral organ identity gene AP3 (Sakai et al., "Role of SUPERMAN in Maintaining Arabidopsis Floral Whorl Boundaries," Nature 378:199–203 (1995)), is important in ovule integument development (Gaiser et al., "The Arabidopsis SUPERMAN Gene Mediates Asymmetric Growth of the Outer Integument of Ovules," The Plant Cell 7:333–345 (1995)). The organ identity gene AP2 is also known to control ovule morphogenesis (Modrusan et al., "Homeotic Transformation of Ovules into Carpel-Like Structures in Arabidopsis," The Plant Cell 6:333–349 (1994)). By contrast, no known meristem identity or flowering control gene had, until now, been demonstrated to have a role in ovule development.

A gene termed SHORT INTEGUMENTS1 (SIN1), genetically detected in the model plant Arabidopsis thaliana by mutational studies has been determined to be an important regulatory gene for plant reproductive development. The SIN1 gene is required for normal ovule development (Lang et al., "sin1, A Mutation Affecting Female Fertility in Arabidopsis, Interacts with mod1, its Recessive Modifier," Genetics 137:1101–1110 (1994); Reiser et al., "The Ovule and the Embryo Sac," The Plant Cell 5:1291–1301 (1993); Robinson-Beers et al., "Ovule Development in Wild-Type Arabidopsis and Two Female Sterile Mutants," Plant Cell 4:1237–1250 (1992)). The original isolate of the sin1 mutation (sin1-1 allele) was identified as one causing a female sterile phenotype (Robinson-Beers et al., "Ovule Development in Wild-Type Arabidopsis and Two Female Sterile Mutants," Plant Cell 4:1237–1250 (1992)). Ovules of the original isolate have short integuments and a defective megagametophyte (see Reiser et al., "The Ovule and the Embryo Sac," The Plant Cell 5: 1291–1301 (1993)) for a review on ovule structure; Baker et al., "Interactions Among Genes Regulating Ovule Development in Arabidopsis thaliana," Genetics 145:1109–1124 (1997), for a recent genetic analysis; Schneitz et al., "Dissection of Sexual Organ Ontogenesis: A Genetic Analysis of Ovule Development in Arabidopsis thaliana," Development 124:1367–1376 (1997), for a summary of the known mutants affected in ovule development). It has been shown that the originally-described Sin1⁻ mutant phenotype is a result of an interaction between sin1, and mod1, its recessive modifier (Lang et al., "sin1, A Mutation Affecting Female Fertility in Arabidopsis, Interacts with mod1, Its Recessive Modifier," Genetics 137:1101–1110 (1994)), and that mod1 is erecta, a mutation in a putative serine-threonine receptor protein kinase gene. The sin1-1 or sin1-2 mutation acting alone causes a defect in the coordination of growth of the two sheets of cells of the inner and outer integuments. All other originally described effects on the ovule, such as the lack of outer integument cell expansion and arrest of the megagametophyte, are due to secondary genetic interactions with erecta. There are several prospective protein phosphorylation sites within the SIN1 protein, and these might be substrates of protein kinases, such as the ERECTA product (Torii et al., "The Arabidopsis ERECTA Gene Encodes a Putative Protein Kinase with Extracellular Leucine-Rich Repeats," Plant Cell 8:735–746 (1996)).

In plants homozygous for the weaker sin1-2 mutant allele, approximately 40% of all ovules in any flower mature into seeds. But these seeds frequently contain embryos arrested at different stages of development, some of which germinate to produce abnormal seedlings. Genetic analysis shows that the maternal expression of the SIN1 gene is necessary for embryo development (Ray et al., "Maternal Effects of the Short Integument Mutation on Embryo Development in Arabidopsis," *Dev. Biol.* 180:365–369 (1996)).

Not only does this gene function in the formation of seeds, SIN1 is the only identified plant gene whose maternal expression is important for pattern formation in the zygotic embryo (Ray et al., "Maternal Effects of the Short Integument Mutation on Embryo Development in Arabidopsis," *Dev. Biol.* 180:365–369 (1996)). Both sin1-1 and sin1-2 alleles have the maternal-effect embryonic lethality phenotype (Ray et al., "Maternal Effects of the Short Integument Mutation on Embryo Development in Arabidopsis," *Dev. Biol.* 180:365–369 (1996)). The wild type SIN1 allele when transmitted through the pollen is unable to rescue the deleterious effects on embryogenesis of a homozygous maternal sin1-2 mutation. Ray et al. have shown that a wild type allele of SIN1 in the endosperm cannot rescue the maternal-effect of sin1-2 (Ray et al., "Maternal Effects of the Short Integument Mutation on Embryo Development in Arabidopsis," *Dev. Biol.* 180:365–369 (1996)). This is the first demonstration of a maternal effect embryonic pattern formation gene in a plant.

In *Arabidopsis thaliana*, meristem development progresses through at least three distinct phases: from vegetative (V) through inflorescence (I) to the floral (F) mode, a process known as the "V→I→F switch." It has been shown that the sin1 mutation causes a defect in the V→I→F switch. SIN1 is needed for the expression of the early flowering phenotype imparted by a TERMINAL FLOWER1 (tfl1) mutation, and tfl1 sin1 double mutants do not produce pollen. Furthermore, sin1-1 allele enhances the effect of an APETALA1 (ap1) mutation. Thus, SIN1 represents a genetic connection between ovule development and control of flowering.

In addition, the function of SIN1 gene is important for controlling the time to flower, another important agronomic factor because the timing of seed production depends on the flowering time. Ray et al. have shown by genetic analysis that SIN1 gene regulates the activity of a master switch gene, LEAFY (LFY) that controls flowering time in *Arabidopsis thaliana*. The LEAFY gene from *Arabidopsis thaliana* was shown to accelerate the flowering time of aspen (an economically important timber plant) from many years to a few months. Additionally, sin1 mutants are late flowering (Ray et al., "SHORT INTEGUEMNT (sin1), A Gene Required For Ovule Development in Arabidopsis, Also Controls Flowering Time," *Development* 122, 2631–2638 (1996)) due to the production of an excess of vegetative leaves and lateral inflorescence axes before producing the floral primordia, which suggests a role of SIN1 in meristem fate determination. The ability to improve crop plant production through genetic engineering requires the identification and manipulation of previously unidentified genes that control developmentally important plant processes, including ovule development and flowering in plants.

The present invention is directed to overcoming the deficiencies in the prior art.

SUMMARY OF THE INVENTION

The present invention relates to an isolated nucleic acid molecule encoding a short integuments1 protein.

The present invention also relates to an isolated short integuments1 protein.

The present invention also relates to a method of regulating flowering in plants that involves transducing a plant with a DNA molecule encoding a short integuments1 protein under conditions effective to regulate flowering in the plant.

The present invention also relates to a method of increasing fertility in plants that involves transducing a plant with a DNA molecule encoding a short integuments1 protein under conditions effective to increase fertility.

The present invention also relates to a method of increasing fecundity in plants that involves transducing a plant with a DNA molecule encoding a short integuments 1 protein under conditions effective to increase fecundity.

The present invention also relates to a method of decreasing fertility in plants that involves transducing a plant with a DNA molecule encoding a short integuments1 protein mutated to cause disruption of the DNA molecule under conditions effective to decrease fertility.

The present invention also relates to an expression vector containing a DNA molecule encoding a short integuments1 protein, and plant cells, plant seeds and transgenic plants transformed with a DNA molecule encoding a short integuments1 protein.

It is expected that elucidation of post-transcriptional regulation in plants will contribute significantly to the ability to control plant production through biotechnology. However, very little is currently understood about mechanisms of post-transcriptional controls, especially in plant reproduction. This invention overcomes this and other deficiencies in the art, as the SIN1 gene and its encoded protein, which play a vital role in fertility, seed production and flowering time control in plants, provide the agronomist with important tools for engineering the expression of genes involved in seed/embryo development and flowering time.

DETAILED DESCRIPTION OF THE INVENTION

Figure 1:
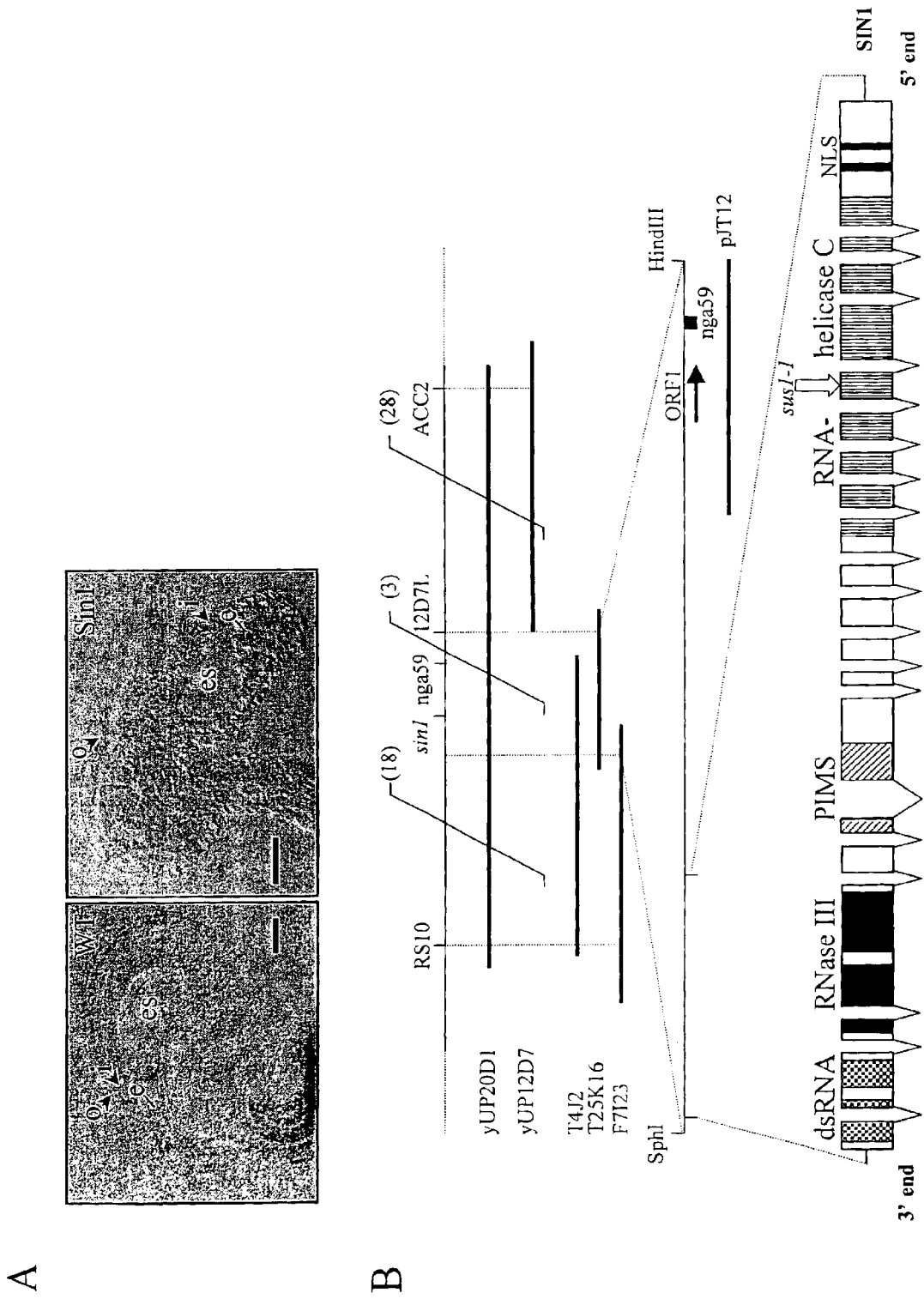
FIG. 1 is a map of the chromosomal region overlapping SIN1 and the functional domains of the predicted SIN1 protein.

The present invention relates to an isolated nucleic acid molecule encoding a short integuments1 (SIN1) protein.

One example of the nucleic acid molecule of the present invention is the SIN1 cDNA molecule, isolated from *Arabidopsis thaliana*, which has a nucleotide sequence corresponding to SEQ. ID. No. 1 as follows:

```
gaagacgaag agagaaacag aacagagtag ggatcgatag accgtggaat ctcagaatca      60
caaacacttt gcaaaagggt tttcaattcc tatttattta caaagaaatc atcaatagta     120
gtggtctcta gggttttgct tgctcttctt cgtgacccct ttttacctgc aaacaacaac     180
ttcaaaattg gcgtgtttcg tacggtctat ctaaccctaa tctgtcacaa aacactcttc     240
ttctctcacc ccttttctg ggtttattca attctcgtgc ttttggttct gttttcttct     300
ctggggattt ggttttcttg agtgagtttt tctcctcttt cttatgttct tgatttgatt     360
attatataga attatggtaa tggaggatga gcctagagaa gccacaataa agccttctta     420
ttggctagat gcttgcgagg acatctcttg tgatcttatc gatgatctcg tgtctgaatt     480
tgatccttcc tctgttgctg tcaatgaatc cactgatgaa aacggcgtca tcaatgattt     540
tttcggtggg attgatcaca ttttagatag tatcaagaac ggtggaggct taccaaacaa     600
tggcgtttct gataccaatt ctcaaatcaa cgaggttact gtaactcctc aggttattgc     660
taaggagaca gtgaaggaga atgggttgca aagaatggc ggtaagagag acgaattctc     720
gaaagaggaa ggagacaagg ataggaagag agctagggtt tgtagttatc agagtgaaag     780
gagtaacctt tcaggtagag ggcatgttaa taattctagg gagggagata ggtttatgaa     840
taggaaacgt actcgtaatt gggacgaggc gggtaacaat aagaagaaaa gggaatgtaa     900
caattacaga agagatggta gagatagaga agttagggggg tattgggaga gggataaagt     960
tggttccaat gagttggttt ataggtcagg gacttgggaa gctgatcatg aaagagatgt    1020
taagaaagtg agtggtggaa accgcgaatg cgatgtcaag gcagaggaga acaagagtaa    1080
gcctgaagaa cgtaaagaga aggttgtgga agagcaagca aggcgatacc agttggatgt    1140
tcttgaacaa gctaaagcga aaaacacgat tgctttcctt gagaccggtg ctggaaagac    1200
acttatcgcg attcttctta ttaaaagtgt tcataaggat ctgatgagcc agaacagaaa    1260
aatgctctcg gtgttcttgg ttcccaaagt gcctttggtt tatcagcaag cagaagtgat    1320
ccgtaatcaa acttgttttc aagttggaca ttattgtggt gagatgggac aggacttttg    1380
ggattctcga aggtggcaac gagagtttga gtctaagcag gttctagtta tgacagcaca    1440
aattctgttg aatatactga gacacagtat cattagaatg gaaacaattg atcttcttat    1500
tctcgacgag tgtcaccacg ctgtcaagaa acatccatac tctttagtga tgtcagagtt    1560
ttaccataca actcctaaag ataaaagacc tgccatcttt ggaatgactg cttcgcctgt    1620
taatttaaag ggtgtttcaa gccaagtaga ttgtgcgata aagatacgta acctcgagac    1680
caagttggat tctacggttt gtactataaa agatcgaaaa gaattagaga aacatgtgcc    1740
tatgccttca gagatagtcg tcgagtatga caaagctgct actatgtggt ctcttcatga    1800
gacaataaag caaatgattg cagctgttga agaagcggca caagcaagtt caaggaaaag    1860
caagtggcaa tttatggggg ctagggatgc tggagcaaag gatgaattga gacaggttta    1920
tggcgtctct gaaagaacgg agagcgatgg tgctgccaat ttgattcata aacttagagc    1980
tatcaattat actcttgctg aattgggtca atggtgtgct acaaggtgg acaatcatt    2040
cttgtctgct ttgcaaagtg atgagagggt gaatttccaa gtcgacgtga agtttcaaga    2100
atcataccct cagtgaggtgg tgtcactctt gcaatgtgag cttctggaag gcgctgctgc    2160
tgaaaaagtc gcggcggaag ttggcaaacc agaaaatggt aatgcacatg acgagatgga    2220
ggagggagag ctccctgatg atcctgtggt ctcgggaggg gagcacgttg atgaagtaat    2280
aggcgccgca gtggctgatg ggaaagttac tccaaaagta caatcattga tcaaactact    2340
cctcaaatat cagcacacag ctgattttcg agctattgtt ttcgttgaga gggtggttgc    2400
```

-continued

```
tgctttggtt cttcctaagg tttttgcgga gctgccttcg cttagtttta tacggtgtgc    2460
cagcatgatt ggacacaata acagccagga gatgaaatca tctcaaatgc aggatacaat    2520
ttccaaattc cgagatgggc atgtgacact gttagttgcc acaagcgttg ctgaggaagg    2580
acttgatatt aggcaatgta acgttgttat gcgtttcgac cttgcaaaga cggtgctggc    2640
atacattcag tctcgtggcc gggcaagaaa gcctggatca gactacatac tcatggttga    2700
gagaggaaat gtatctcacg cagcgttcct aaggaatgct aggaacagtg aggagacact    2760
tcgaaaagaa gcaatagaaa ggactgatct tagtcatctc aaagatacat cgagattaat    2820
ctcaattgat gctgtgcctg gtacagttta aaggtggag gcaactggtg ccatggttag     2880
cttgaattcc gcggttggtc ttgtacattt ctactgctct cagcttcctg gtgacaggta    2940
tgcaatcctt cgtcctgagt ttagcatgga gaagcatgaa aagcctgggg ccacacggaa    3000
atattcatgt aggcttcagc ttccttgcaa tgcaccgttt gaaatacttg agggtcctgt    3060
ttgcagttca atgcgtcttg cacaacaggc tgtatgttta gctgcttgca gaaactgca    3120
tgagatgggt gcatttaccg atatgctatt accggacaaa ggaagtggtc aagacgctga    3180
gaaggctgac caagatgatg aaggtgagcc tgttcctgga actgctagac atagagagtt    3240
ctatcctgaa ggtgtggcgg atgtacttaa gggagaatgg gtttcatctg gaaaggaagt    3300
ttgtgagagc tcaaagctat tccatttata catgtataat gtcagatgtg tagattttgg    3360
ctcttcaaaa gatccattcc taagcgaagt ttcagagttc gcgattcttt ttggcaatga    3420
gctggatgca gaggtattat cgatgtctat ggatctttat gttgctcggg ccatgatcac    3480
taaagcatct cttgctttca agggatcact tgatattaca gaaaaccagc tatcatctct    3540
aaaaaagttt catgtgaggt taatgagtat cgtgttggat gttgatgttg aaccctccac    3600
gacaccatgg gatcctgcaa aggcctacct gttttgtccct gttactgaca atacgtctat    3660
ggaacccata aaagggatca actgggaatt ggttgaaaag attacgaaaa ccacagcgtg    3720
ggacaaccct cttcagagag ctcgtcccga tgtatatctc gggactaatg agagaactct    3780
tggtggggac agaagggaat atgggtttgg taaacttcgt cacaacattg tatttgggca    3840
gaaatctcac ccaacttatg gtattagagg agctgttgca tccttcgatg ttgtgagagc    3900
ttctggattg ttacctgtga gagatgcttt tgagaaggaa gtagaagagg atttatcaaa    3960
aggaaaattg atgatggctg atgggtgcat ggttgcagaa gatcttattg ggaaaatagt    4020
gacagccgca cattccggga agcgttttta cgtagattca atttgttatg acatgagtgc    4080
agaaacatct ttccctagga aagagggata tcttggtccc ctagagtaca acacgtacgc    4140
tgactattac aagcaaaagt atggagttga tttgaactgt aagcaacaac ctttgattaa    4200
aggacgtggt gtttcgtatt gcaagaacct tctttctcct cggtttgaac agtcaggtga    4260
atctgagaca gtccttgata agacatatta cgtgtttctt ccacctgaac tatgcgttgt    4320
gcatccgctt tcgggttcac ttatccgagg tgctcagagg ttaccctcta taatgagaag    4380
agttgagagc atgttactcg ctgttcaact caaaaatttg attagttatc ctattcccac    4440
atcaaagatt cttgaagcct tgactgccgc ctcgtgccag gaaacgttct gctacgagag    4500
agctgagctt ttaggagatg cgtatctaaa atgggttgtt agtcgttttc tgtttctcaa    4560
gtatcctcaa aagcacgagg gtcagcttac aaggatgagg caacaaatgg ttagtaatat    4620
ggttctttat cagtttgctc tggttaaagg gcttcagtca tatatccagg cggatcgatt    4680
cgccccgtct agtggtcctg ctcctggtgt gcctccggtt ttcgacgagg acacaaaaga    4740
tggaggatct tcgttttcg atgaagagca aaaacctgtt tccgaggaaa acagcgatgt    4800
```

```
                                    -continued
gttttgaagat ggggagatgg aggatggtga actagagggt gatttgagtt cgtaccgagt    4860
tttatctagc aaaacgttag ctgatgttgt tgaggctttg attggtgttt attacgtcga    4920 aggggggtaag attgcagcta atcatttgat gaaatggatt gggattcacg tggaggatga    4980
tcctgatgaa gtcgatggaa cattgaaaaa tgttaatgtt ccagagagtg tgctcaagag    5040
catcgacttt gttggtcttg agagagctct taaatatgag tttaaagaga aaggtcttct    5100
tgttgaagct ataacacatg cttcaagacc atcttcaggt gtttcgtgtt accagagatt    5160
ggaatttgtt ggtgacgcgg tcttggatca tctcatcaca agacatctat ttttcacata    5220
cacaagcctt cctcctggtc ggttaacaga tcttcgagct gcagcggtta acaacgagaa    5280
ttttgctcgc gttgcggtta aacataaact ccacttgtac cttcgtcacg gttcaagcgc    5340
cctcgaaaaa cagattcggg aatttgtgaa ggaggttcaa accgagtcat cgaaaccggg    5400
gtttaactct tttggtttgg gagactgcaa accaccaaaa gttcttggag acattgttga    5460
atctattgca ggtgctatt ttcttgatag tggaaaagat acaactgctg cttggaaggt    5520
ttttcaacct ttgcttcagc ccatggtgac accagagaca cttccaatgc atccggtgcg    5580
agagctacaa gagcggtgcc agcaacaagc agaagggtta gaatacaaag cgagtaggag    5640
tggtaacaca gcgactgtgg aagttttcat cgacggtgtt caagttggag tagcgcaaaa    5700
cccgcagaag aaaatggctc aaaagctagc tgcgaggaac gcacttgcag ctttgaaaga    5760
gaaagaaata gcagaatcaa aggagaagca tatcaacaac ggtaatgcgg gagaggatca    5820
aggcgagaat gagaatggga acaagaagaa tgggcatcag ccgtttacga gacaaacgtt    5880
gaatgatatt tgtttgagga agaattggcc aatgccttct tacagatgtg tgaaagaagg    5940
aggaccggct catgcaaaga gatttacgtt tggggtaaga gttaatacga gcgatagagg    6000
atggaccgat gagtgtattg gcgagccaat gccgagtgtt aagaaagcta aggattcagc    6060
tgcggttctt ctacttgagc ttttaaataa aactttttct tgattctttt actctcttca    6120
acgagatgta gtcattacat tttaaacctt aaaaccatag tggttgtagt gttttaaaaa    6180
aaaa                                                                 6184
```

The isolated cDNA has a 5727 bp open reading frame (ORF), a 374 bp 5'-untranslated region (UTR), a 74 bp 3'-UTR and nine adenines at the 3'-end likely to be from the poly-A tail. The cDNA sequence confirmed the presence of 19 introns and 20 exons. A map of the chromosomal region overlapping SIN1 is shown in FIG. 1. RS10, nga59, 12D7L and ACC2 are DNA sequence markers. Numbers within brackets are numbers of cross-overs between La-er and Columbia chromosomes. yUP20D1 and yUP12D7 are YAC clones; T4J2, T25K16 and F7I23 are BAC clones. The lower portion of the diagram shows intron-exon boundaries of SIN1 gene. The arrow above the sus1-1 shows that site of insertion of the linked T-DNA in sus1-1. That the open reading frame corresponds to SIN1 gene is substantiated by the findings that the sus1, sin1-1, and sin1-2 mutant phenotypes are traceable to DNA mutations in the SIN1 gene. The sus1 mutation is due to DNA insertion within the 5th exon of the SIN1 gene. The sin1-1 and sin1-2 phenotypes are the result of single-base pair changes, in exon 3 and exon 4, respectively. A single C to T transition in sin1-1 and a T to A transversion in sin1-2 reading frames were detected.

Also suitable as an isolated nucleic acid molecule according to the present invention is a nucleic acid which has a nucleotide sequence that is at least 55% similar to the nucleotide sequence of SEQ. ID. No. 1 by basic BLAST using default parameters analysis. Also suitable as an isolated nucleic acid molecule according to the present invention is an isolated nucleic acid molecule encoding a short integuments1 protein, wherein the nucleic acid hybridizes to the nucleotide sequence of SEQ. ID. No. 1 under stringent conditions characterized by a hybridization buffer comprising 0.9M sodium citrate buffer at a temperature of 45° C.

The nucleotide sequence of SEQ. ID. NO. 1 encodes a protein having an amino acid sequence corresponding to SEQ. ID. No. 2, as follows:

```
Met Val Met Glu Asp Glu Pro Arg Glu Ala Thr Ile Lys Pro Ser Tyr
 1               5                  10                  15

Trp Leu Asp Ala Cys Glu Asp Ile Ser Cys Asp Leu Ile Asp Asp Leu
            20                  25                  30
```

-continued

```
Val Ser Glu Phe Asp Pro Ser Ser Val Ala Val Asn Glu Ser Thr Asp
         35                  40                  45

Glu Asn Gly Val Ile Asn Asp Phe Phe Gly Gly Ile Asp His Ile Leu
 50                  55                  60

Asp Ser Ile Lys Asn Gly Gly Leu Pro Asn Asn Gly Val Ser Asp
 65                  70                  75                  80

Thr Asn Ser Gln Ile Asn Glu Val Thr Val Thr Pro Gln Val Ile Ala
             85                  90                  95

Lys Glu Thr Val Lys Glu Asn Gly Leu Gln Lys Asn Gly Gly Lys Arg
             100                 105                 110

Asp Glu Phe Ser Lys Glu Glu Gly Asp Lys Asp Arg Lys Ala Arg
             115                 120                 125

Val Cys Ser Tyr Gln Ser Glu Arg Ser Asn Leu Ser Gly Arg Gly His
     130                 135                 140

Val Asn Asn Ser Arg Glu Gly Asp Arg Phe Met Asn Arg Lys Arg Thr
145                 150                 155                 160

Arg Asn Trp Asp Glu Ala Gly Asn Asn Lys Lys Lys Arg Glu Cys Asn
                 165                 170                 175

Asn Tyr Arg Arg Asp Gly Arg Asp Arg Glu Val Arg Gly Tyr Trp Glu
                 160                 185                 190

Arg Asp Lys Val Gly Ser Asn Glu Leu Val Tyr Arg Ser Gly Thr Trp
             195                 200                 205

Glu Ala Asp His Glu Arg Asp Val Lys Lys Val Ser Gly Gly Asn Arg
     210                 215                 220

Glu Cys Asp Val Lys Ala Glu Glu Asn Lys Ser Lys Pro Glu Glu Arg
225                 230                 235                 240

Lys Glu Lys Val Val Glu Glu Gln Ala Arg Arg Tyr Gln Leu Asp Val
                 245                 250                 255

Leu Glu Gln Ala Lys Ala Lys Asn Thr Ile Ala Phe Leu Glu Thr Gly
             260                 265                 270

Ala Gly Lys Thr Leu Ile Ala Ile Leu Leu Ile Lys Ser Val His Lys
     275                 280                 285

Asp Leu Met Ser Gln Asn Arg Lys Met Leu Ser Val Phe Leu Val Pro
290                 295                 300

Lys Val Pro Leu Val Tyr Gln Gln Ala Glu Val Ile Arg Asn Gln Thr
305                 310                 315                 320

Cys Phe Gln Val Gly His Tyr Cys Gly Glu Met Gly Gln Asp Phe Trp
                 325                 330                 335

Asp Ser Arg Arg Trp Gln Arg Glu Phe Glu Ser Lys Gln Val Leu Val
             340                 345                 350

Met Thr Ala Gln Ile Leu Leu Asn Ile Leu Arg His Ser Ile Ile Arg
     355                 360                 365

Met Glu Thr Ile Asp Leu Leu Ile Leu Asp Glu Cys His His Ala Val
     370                 375                 380

Lys Lys His Pro Tyr Ser Leu Val Met Ser Glu Phe Tyr His Thr Thr
385                 390                 395                 400

Pro Lys Asp Lys Arg Pro Ala Ile Phe Gly Met Thr Ala Ser Pro Val
                 405                 410                 415

Asn Leu Lys Gly Val Ser Ser Gln Val Asp Cys Ala Ile Lys Ile Arg
             420                 425                 430

Asn Leu Glu Thr Lys Leu Asp Ser Thr Val Cys Thr Ile Lys Asp Arg
     435                 440                 445

Lys Glu Leu Glu Lys His Val Pro Met Pro Ser Glu Ile Val Val Glu
```

-continued

```
            450                 455                   460
Tyr Asp Lys Ala Ala Thr Met Trp Ser Leu His Glu Thr Ile Lys Gln
465                 470                  475                 480

Met Ile Ala Ala Val Glu Glu Ala Ala Gln Ala Ser Ser Arg Lys Ser
                    485                  490                 495

Lys Trp Gln Phe Met Gly Ala Arg Asp Ala Gly Ala Lys Asp Glu Leu
                500                  505                 510

Arg Gln Val Tyr Gly Val Ser Glu Arg Thr Glu Ser Asp Gly Ala Ala
            515                  520                 525

Asn Leu Ile His Lys Leu Arg Ala Ile Asn Tyr Thr Leu Ala Glu Leu
        530                  535                 540

Gly Gln Trp Cys Ala Tyr Lys Val Gly Gln Ser Phe Leu Ser Ala Leu
545                 550                  555                 560

Gln Ser Asp Glu Arg Val Asn Phe Gln Val Asp Val Lys Phe Gln Glu
                565                  570                 575

Ser Tyr Leu Ser Glu Val Val Ser Leu Leu Gln Cys Glu Leu Leu Glu
            580                  585                 590

Gly Ala Ala Ala Glu Lys Val Ala Ala Glu Val Gly Lys Pro Glu Asn
            595                  600                 605

Gly Asn Ala His Asp Glu Met Glu Glu Gly Glu Leu Pro Asp Asp Pro
        610                  615                 620

Val Val Ser Gly Gly Glu His Val Asp Glu Val Ile Gly Ala Ala Val
625                 630                  635                 640

Ala Asp Gly Lys Val Thr Pro Lys Val Gln Ser Leu Ile Lys Leu Leu
                645                  650                 655

Leu Lys Tyr Gln His Thr Ala Asp Phe Arg Ala Ile Val Phe Val Glu
                660                  665                 670

Arg Val Ala Ala Leu Val Leu Pro Lys Val Phe Ala Glu Leu Pro
            675                  680                 665

Ser Leu Ser Phe Ile Arg Cys Ala Ser Met Ile Gly His Asn Asn Ser
            690                  695                 700

Gln Glu Met Lys Ser Ser Gln Met Gln Asp Thr Ile Ser Lys Phe Arg
705                 710                  715                 720

Asp Gly His Val Thr Leu Leu Val Ala Thr Ser Val Ala Glu Glu Gly
                725                  730                 735

Leu Asp Ile Arg Gln Cys Asn Val Val Met Arg Phe Asp Leu Ala Lys
                740                  745                 750

Thr Val Leu Ala Tyr Ile Gln Ser Arg Gly Arg Ala Arg Lys Pro Gly
            755                  760                 765

Ser Asp Tyr Ile Leu Met Val Glu Arg Gly Asn Val Ser His Ala Ala
        770                  775                 780

Phe Leu Arg Asn Ala Arg Asn Ser Glu Glu Thr Leu Arg Lys Glu Ala
785                 790                  795                 800

Ile Glu Arg Thr Asp Leu Ser His Leu Lys Asp Thr Ser Arg Leu Ile
                805                  810                 815

Ser Ile Asp Ala Val Pro Gly Thr Val Tyr Lys Val Glu Ala Thr Gly
                820                  825                 830

Ala Met Val Ser Leu Asn Ser Ala Val Gly Leu Val His Phe Tyr Cys
            835                  840                 845

Ser Gln Leu Pro Gly Asp Arg Tyr Ala Ile Leu Arg Pro Glu Phe Ser
        850                  855                 860

Met Glu Lys His Glu Lys Pro Gly Gly Thr Glu Tyr Ser Cys Arg
865                 870                  875                 880
```

-continued

Leu Gln Leu Pro Cys Asn Ala Pro Phe Glu Ile Leu Glu Gly Pro Val
            885                 890                 895

Cys Ser Ser Met Arg Leu Ala Gln Gln Ala Val Cys Leu Ala Ala Cys
            900                 905                 910

Lys Lys Leu His Glu Met Gly Ala Phe Thr Asp Met Leu Leu Pro Asp
            915                 920                 925

Lys Gly Ser Gly Gln Asp Ala Glu Lys Ala Asp Gln Asp Asp Glu Gly
            930                 935                 940

Glu Pro Val Pro Gly Thr Ala Arg His Arg Glu Phe Tyr Pro Glu Gly
945                 950                 955                 960

Val Ala Asp Val Leu Lys Gly Glu Trp Val Ser Ser Gly Lys Glu Val
            965                 970                 975

Cys Glu Ser Ser Lys Leu Phe His Leu Tyr Met Tyr Asn Val Arg Cys
            980                 985                 990

Val Asp Phe Gly Ser Ser Lys Asp Pro Phe Leu Ser Glu Val Ser Glu
            995                 1000                1005

Phe Ala Ile Leu Phe Gly Asn Glu Leu Asp Ala Glu Val Leu Ser Met
            1010                1015                1020

Ser Met Asp Leu Tyr Val Ala Arg Ala Met Ile Thr Lys Ala Ser Leu
1025                1030                1035                1040

Ala Phe Lys Gly Ser Leu Asp Ile Thr Glu Asn Gln Leu Ser Ser Leu
            1045                1050                1055

Lys Lys Phe His Val Arg Leu Met Ser Ile Val Leu Asp Val Asp Val
            1060                1065                1070

Glu Pro ser Thr Thr Pro Trp Asp Pro Ala Lys Ala Tyr Leu Phe Val
            1075                1080                1085

Pro Val Thr Asp Asn Thr Ser Met Glu Pro Ile Lys Gly Ile Asn Trp
            1090                1095                1100

Glu Leu Val Glu Lys Ile Thr Lys Thr Ala Trp Asp Asn Pro Leu
1105                1110                1115                1120

Gln Arg Ala Arg Pro Asp Val Tyr Leu Gly Thr Asn Glu Arg Thr Leu
            1125                1130                1135

Gly Gly Asp Arg Arg Glu Tyr Gly Phe Gly Lys Leu Arg His Asn Ile
            1140                1145                1150

Val Phe Gly Gln Lys Ser His Pro Thr Tyr Gly Ile Arg Gly Ala Val
            1155                1160                1165

Ala Ser Phe Asp Val Val Arg Ala Ser Gly Leu Leu Pro Val Arg Asp
            1170                1175                1180

Ala Phe Glu Lys Glu Val Glu Glu Asp Leu Ser Lys Gly Lys Leu Met
1185                1190                1195                1200

Met Ala Asp Gly Cys Met Val Ala Glu Asp Leu Ile Gly Lys Ile Val
            1205                1210                1215

Thr Ala Ala His Ser Gly Lys Arg Phe Tyr Val Asp Ser Ile Cys Tyr
            1220                1225                1230

Asp Met Ser Ala Glu Thr Ser Phe Pro Arg Lys Glu Gly Tyr Leu Gly
            1235                1240                1245

Pro Leu Glu Tyr Asn Thr Tyr Ala Asp Tyr Tyr Lys Gln Lys Tyr Gly
            1250                1255                1260

Val Asp Leu Asn Cys Lys Gln Gln Pro Leu Ile Lys Gly Arg Gly Val
1265                1270                1275                1280

Ser Tyr Cys Lys Asn Leu Leu Ser Pro Arg Phe Glu Gln Ser Gly Glu
            1285                1290                1295

Ser Glu Thr Val Leu Asp Lys Thr Tyr Tyr Val Phe Leu Pro Pro Glu
            1360                1305                1310

-continued

```
Leu Cys Val Val His Pro Leu Ser Gly Ser Leu Ile Arg Gly Ala Gln
    1315                1320                1325

Arg Leu Pro Ser Ile Met Arg Arg Val Glu Ser Met Leu Leu Ala Val
    1330                1335                1340

Gln Leu Lys Asn Leu Ile Ser Tyr Pro Ile Pro Thr Ser Lys Ile Leu
1345                1350                1355                1360

Glu Ala Leu Thr Ala Ala Ser Cys Gln Glu Thr Phe Cys Tyr Glu Arg
            1365                1370                1375

Ala Glu Leu Leu Gly Asp Ala Tyr Leu Lys Trp Val Val Ser Arg Phe
        1380                1385                1390

Leu Phe Leu Lys Tyr Pro Gln Lys His Glu Gly Gln Leu Thr Arg Met
    1395                1400                1405

Arg Gln Gln Met Val Ser Asn Met Val Leu Tyr Gln Phe Ala Leu Val
    1410                1415                1420

Lys Gly Leu Gln Ser Tyr Ile Gln Ala Asp Arg Phe Ala Pro Ser Arg
1425                1430                1435                1440

Trp Ser Ala Pro Gly Val Pro Pro Val Phe Asp Glu Asp Thr Lys Asp
            1445                1450                1455

Gly Gly Ser Ser Phe Phe Asp Glu Glu Gln Lys Pro Val Ser Glu Glu
        1460                1465                1470

Asn Ser Asp Val Phe Glu Asp Gly Glu Met Glu Asp Gly Glu Leu Glu
    1475                1480                1485

Gly Asp Leu Ser Ser Tyr Arg Val Leu Ser Ser Lys Thr Leu Ala Asp
    1490                1495                1500

Val Val Glu Ala Leu Ile Gly Val Tyr Tyr Val Glu Gly Gly Lys Ile
1505                1510                1515                1520

Ala Ala Asn His Leu Met Lys Trp Ile Gly Ile His Val Glu Asp Asp
            1525                1530                1535

Pro Asp Glu Val Asp Gly Thr Leu Lys Asn Val Asn Val Pro Glu Ser
        1540                1545                1550

Val Leu Lys Ser Ile Asp Phe Val Gly Leu Glu Arg Ala Leu Lys Tyr
    1555                1560                1565

Glu Phe Lys Glu Lys Gly Leu Leu Val Glu Ala Ile Thr His Ala Ser
    1570                1575                1580

Arg Pro Ser Ser Gly Val Ser Cys Tyr Gln Arg Leu Glu Phe Val Gly
1585                1590                1595                1600

Asp Ala Val Leu Asp His Leu Ile Thr Arg His Leu Phe Phe Thr Tyr
            1605                1610                1615

Thr Ser Leu Pro Pro Gly Arg Leu Thr Asp Leu Arg Ala Ala Ala Val
        1620                1625                1630

Asn Asn Glu Asn Phe Ala Arg Val Ala Val Lys His Lys Leu His Leu
    1635                1640                1645

Tyr Leu Arg His Gly Ser Ser Ala Leu Glu Lys Gln Ile Arg Glu Phe
    1650                1655                1660

Val Lys Glu Val Gln Thr Glu Ser Ser Lys Pro Gly Phe Asn Ser Phe
1665                1670                1675                1680

Gly Leu Gly Asp Cys Lys Ala Pro Lys Val Leu Gly Asp Ile Val Glu
            1685                1690                1695

Ser Ile Ala Gly Ala Ile Phe Leu Asp Ser Gly Lys Asp Thr Thr Ala
        1700                1705                1710

Ala Trp Lys Val Phe Gln Pro Leu Leu Gln Pro Met Val Thr Pro Glu
    1715                1720                1725

Thr Leu Pro Met His Pro Val Arg Glu Leu Gln Glu Arg Cys Gln Gln
```

-continued

```
         1730              1735              1740
Gln Ala Glu Gly Leu Glu Tyr Lys Ala Ser Arg Ser Gly Asn Thr Ala
1745                1750                1755                1760

Thr Val Glu Val Phe Ile Asp Gly Val Gln Val Gly Val Ala Gln Asn
                1765                1770                1775

Pro Gln Lys Lys Met Ala Gln Lys Leu Ala Ala Arg Asn Ala Leu Ala
        1780                1785                1790

Ala Leu Lys Glu Lys Glu Ile Ala Glu Ser Lys Glu Lys His Ile Asn
        1795                1800                1805

Asn Gly Asn Ala Gly Glu Asp Gln Gly Glu Asn Glu Asn Gly Asn Lys
    1810                1815                1820

Lys Asn Gly His Gln Pro Phe Thr Arg Gln Thr Leu Asn Asp Ile Cys
1825                1830                1835                1840

Leu Arg Lys Asn Trp Pro Met Pro Ser Tyr Arg Cys Val Lys Glu Gly
                1845                1850                1855

Gly Pro Ala His Ala Lys Arg Phe Thr Phe Gly Val Arg Val Asn Thr
            1860                1865                1870

Ser Asp Arg Gly Trp Thr Asp Glu Cys Ile Gly Glu Pro Met Pro Ser
        1875                1880                1885

Val Lys Lys Ala Lys Asp Ser Ala Ala Val Leu Leu Leu Glu Leu Leu
    1890                1895                1900

Asn Lys Thr Phe Ser
1905
```

Figure 2:
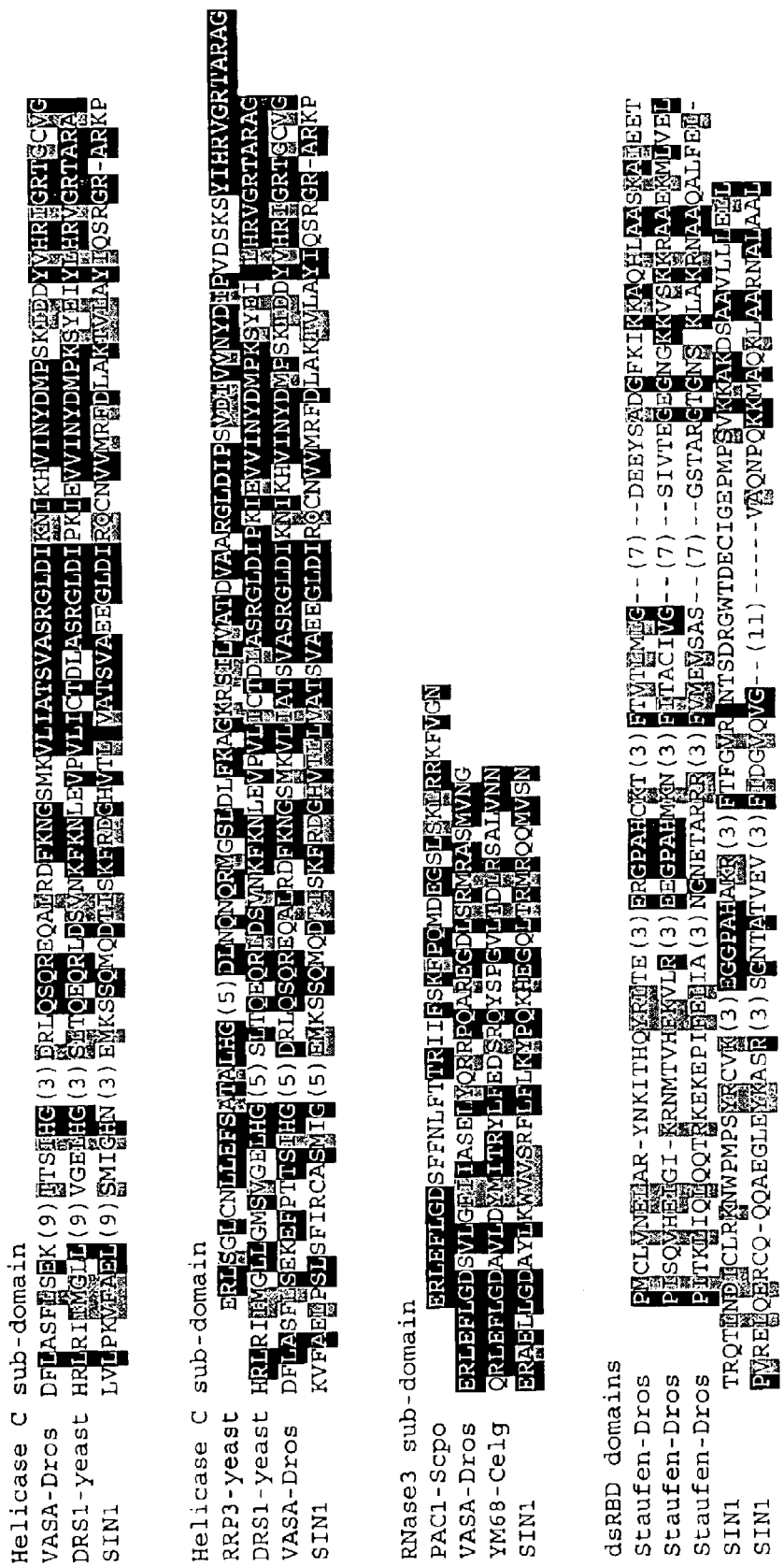
FIG. 2 is a diagram of the BLAST derived homologies of the SIN1 protein, as follows: helicase C domains of SIN1 (SEQ ID NO: 5 and SEQ ID NO: 9) compared to yeast DRSI (SEQ ID NO: 4 and SEQ ID NO: 7), yeast RRP3 (SEQ ID NO: 6), and Drosophila Vasa products (SEQ ID NO: 3 and SEQ ID NO: 8); RNase 3 domain of SIN1 (SEQ ID NO: 13) compared to pombe PAC1 (SEQ ID NO: 10), Drosophila Vasa (SEQ ID NO: 11), and C. elegans YM68 product (SEQ ID NO: 12): and dsRBD domains of SIN1 (SEQ ID NO: 17 and SEQ ID NO: 18) compared to Drosophila Staufen products (SEQ ID NO: 14, SEQ ID NO: 15, and SEQ ID NO: 16).

Analysis of this protein revealed a domain structure highly suggestive of an RNA helicase (Company et al., "Requirement of the RNA Helicase-Like Protein PRP22 for Release of Messenger RNA from Spliceosomes," *Nature* 349:487–493 (1991); Linder et al., "Birth of the D-E-A-D Box," *Nature* 337:121–122 (1989); Luking et al., "The Protein Family of RNA Helicases," *Crit. Rev. Biochem. Mol. Biol.* 33:259–296 (1998); Martins et al., "Mutational Analysis of Vaccinia Virus Nucleoside Triphosphate Phosphohydrolase I, a DNA-Dependent ATPase of the DExH Box Family," *Journal of Virology* 73:1302–1308 (1999), which are hereby incorporated by reference), of which Drosophila maternal effect gene Vasa is a representative (Rongo et al., "Germplasm Assembly and Germ Cell Migration in Drosophila," *Cold Spring Harb. Symp. Quant. Biol.* 62:1–11 (1997), which is hereby incorporated by reference). Shown in the lower portion of FIG. 1 is the arrangement of functional motifs of the predicted SIN1 protein: a bipartite N-terminal nuclear localization signal (NLS), an RNA helicase C domain, two RNase III catalytic domains, a PIMS (for PIWI Middle domain-SHORT INTEGUMENTS1, PIWI being a family of important plant developmental proteins) motif, and two C-terminal repeats of a dsRNA binding domain. A BLAST search yielded numerous high homology strikes of these domains, as shown in FIG. 2. Each of the three functional domains is strongly conserved within its own family. For example, the helicase C motif (SEQ ID NO: 5 and SEQ ID NO: 9) shows strong similarity, among others, to yeast RRP3 (SEQ ID NO: 6), DRS1 (SEQ ID NO: 4 and SEQ ID NO: 7), and fly Vasa products (SEQ ID NO: 3 and SEQ ID NO: 8), RNase3 domains (SEQ ID NO: 13) to pombe PAC1 (SEQ ID NO: 10)or worm K12H4.8 (YM68) (SEQ ID NO: 12), and dsRBD domains (SEQ ID NO: 17 and SEQ ID NO: 18) to Drosophila Staufen products (SEQ ID NO: 14, SEQ ID NO: 15, and SEQ ID NO: 16).

Fragments of the above protein are also encompassed by the present invention. Suitable fragments can be produced by several means. In the first, subclones of the gene encoding the protein of the present invention are produced by conventional molecular genetic manipulation by subcloning gene fragments. The subclones then are expressed in vitro or in vivo in bacterial cells to yield a smaller protein or peptide.

In another approach, based on knowledge of the primary structure of the protein of the present invention, fragments of the gene of the present invention may be synthesized by using the PCR technique together with specific sets of primers chosen to represent particular portions of the protein. These then would be cloned into an appropriate vector for increased expression of an accessory peptide or protein.

Chemical synthesis can also be used to make suitable fragments. Such a synthesis is carried out using known amino acid sequences for the protein of the present invention. These fragments can then be separated by conventional procedures (e.g., chromatography, SDS-PAGE) and used in the methods of the present invention.

Variants may also (or alternatively) be prepared by, for example, the deletion or addition of amino acids that have minimal influence on the properties, secondary structure, and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

The present invention also relates to an expression vector containing a DNA molecule encoding a short integuments1 protein. The nucleic acid molecule of the present invention may be inserted into any of the many available expression vectors and cell systems using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens,* a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTI, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens.* Fraley, et al., "Expression of Bacterial Genes in Plant Cells," *Proc. Nat'l Acad. Sci.,* 80:4803–4807 (1983), which is hereby incorporated by reference.

Further improvement of this technique led to the development of the binary vector system. Bevan, M., "Binary Agrobacterium Vectors for Plant Transformation," *Nucleic Acids Res.* 12:8711–8721 (1984), which is hereby incorporated by reference. In this system, all the T-DNA sequences (including the borders) are removed from the pTi, and a second vector containing T-DNA is introduced into *Agrobacterium tumefaciens.* This second vector has the advantage of being replicable in *E. coli* as well as *A. tumefaciens,* and contains a multiclonal site that facilitates the cloning of a transgene. An example of a commonly used vector is pBin19. Frisch, et al., "Complete Sequence of the Binary Vector Bin19," *Plant Molec. Biol.* 27:405–409 (1995), which is hereby incorporated by reference. Any appropriate vectors now known or later described for genetic transformation are suitable for use with the present invention.

U.S. Pat. No. 4,237,224 issued to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

In one aspect of the present invention, the nucleic acid molecule of the present invention is incorporated into an appropriate vector in the sense direction, such that the open reading frame is properly oriented for the expression of the encoded protein under control of a promoter of choice.

Certain "control elements" or "regulatory sequences" are also incorporated into the vector-construct. Those non-translated regions of the vector, promoters, 5' and 3' untranslated regions-which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase (NOS) gene promoter, from *Agrobacterium tumefaciens,* (U.S. Pat. No. 5,034,322 to Rogers et al., which is hereby incorporated by reference), the cauliflower mosaic virus (CaMv) 35S and 19S promoters (U.S. Pat. No. 5,352,605 to Fraley et al., which is hereby incorporated by reference), those derived from any of the several actin genes, which are known to be expressed in most cells types (U.S. Pat. No. 6,002,068 to Privalle et al., which is hereby incorporated by reference), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.* 88:10421–5 (1991), which is hereby incorporated by reference). Expression of the SIN1 protein is induced in the plants transformed with the SIN1 gene when the transgenic plants are brought into contact with nanomolar concentrations of a glucocorticoid, or by contact with dexamethasone, a glucocorticoid analog. Schena et al., "A Steroid-Inducible Gene Expression System for Plant Cells," *Proc. Natl. Acad. Sci. USA* 88:10421–5 (1991); Aoyama et al., "A Glucocorticoid-Mediated Transcriptional Induction System in Transgenic Plants," *Plant J.* 11: 605–612 (1997), and McNellis et al., "Glucocorticoid-Inducible Expression of a Bacterial Avirulence Gene in Transgenic Arabidopsis Induces Hypersensitive Cell Death, *Plant J.* 14(2):247–57 (1998), which are hereby incorporated by reference. In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 to Shewmaker et al., which is hereby incorporated by reference).

The DNA construct of the present invention also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase 3' regulatory region (Fraley, et al., "Expression of Bacterial Genes in Plant Cells," *Proc. Nat'l Acad. Sci. USA* 80:4803–4807 (1983), which is hereby incorporated by reference) and the cauliflower mosaic virus 3' regulatory region (Odell, et al., "Identification of DNA Sequences Required for Activity of the Cauliflower Mosaic Virus 35S Promoter," *Nature* 313(6005):810–812 (1985), which is hereby incorporated by reference). Virtually any 3' regulatory region known to be operable in plants would suffice for proper expression of the coding sequence of the DNA construct of the present invention.

The vector of choice, promoter, and an appropriate 3' regulatory region can be ligated together to produce the plasmid of the present invention using well known molecular cloning techniques as described in Sambrook et al., *Molecular Cloning: A Laboratory Manual,* Second Edition, Cold Spring Harbor Press, NY (1989), and Ausubel, F. M. et al. (1989) *Current Protocols in Molecular Biology,* John Wiley & Sons, New York, N.Y., which are hereby incorporated by reference.

Once the DNA construct of the present invention has been prepared, it is ready to be incorporated into a host cell. Recombinant molecules can be introduced into cells via transformation, particularly transduction, conjugation, mobilization, or electroporation. The DNA sequences are cloned into the host cell using standard cloning procedures known in the art, as described by Sambrook et al., *Molecular Cloning: A Laboratory Manual,* Second Edition, Cold Springs Laboratory, Cold Springs Harbor, N.Y. (1989), which is hereby incorporated by reference. Suitable host cells include, but are not limited to, bacteria, virus, yeast, mammalian cells, insect, plant, and the like. Preferably the host cells are either a bacterial cell or a plant cell.

Accordingly, another aspect of the present invention relates to a method of making a recombinant cell. Basically, this method is carried out by transforming a plant cell with a DNA construct of the present invention under conditions effective to yield transcription of the DNA molecule in the plant cell. Preferably, the DNA construct of the present invention is stably inserted into the genome of the recombinant plant cell as a result of the transformation.

One approach to transforming plant cells with a DNA construct of the present invention is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford, et al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells. Other variations of particle bombardment, now known or hereafter developed, can also be used.

Transient expression in protoplasts allows quantitative studies of gene expression since the population of cells is very high (on the order of $10^6$). To deliver DNA inside protoplasts, several methodologies have been proposed, but the most common are electroporation (Fromm et al., "Expression of Genes Transferred Into Monocot and Dicot Plants by Electroporation," *Proc. Natl. Acad. Sci. USA* 82:5824–5828 (1985), which is hereby incorporated by reference) and polyethylene glycol (PEG) mediated DNA uptake (Krens et al., "In Vitro Transformation of Plant Protoplasts with Ti-Plasmid DNA," *Nature* 296:72–74 (1982), which is hereby incorporated by reference). During electroporation, the DNA is introduced into the cell by means of a reversible change in the permeability of the cell membrane due to exposure to an electric field. PEG transformation introduces the DNA by changing the elasticity of the membranes. Unlike electroporation, PEG transformation does not require any special equipment and transformation efficiencies can be equally high. Another appropriate method of introducing the gene construct of the present invention into a host cell is fusion of protoplasts with other entities, either minicells, cells, lysosomes, or other fusible lipid-surfaced bodies that contain the chimeric gene. Fraley, et al., *Proc. Natl. Acad. Sci. USA,* 79:1859–63 (1982), which is hereby incorporated by reference.

Stable transformants are preferable for the methods of the present invention. An appropriate method of stably introducing the DNA construct into plant cells is to infect a plant cell with *Agrobacterium tumefaciens* or *Agrobacterium rhizogenes* previously transformed with the DNA construct. Under appropriate conditions known in the art, the transformed plant cells are grown to form shoots or roots, and develop further into plants. In one embodiment of the present invention stable transformants are generated using Agrobacterium using the "dipping" method, a modification of the vacuum infiltration method as described in Bent et al., "Floral Dip: A Simplified Method for Agrobacterium-Mediated Transformation of *Arabidopsis thaliana,*" Plant J. 16:735–43 (1998), which is hereby incorporated by reference.

Plant tissues suitable for transformation include, but are not limited to, floral buds, leaf tissue, root tissue, meristems, zygotic and somatic embryos, megaspores, and anthers.

After transformation, the transformed plant cells can be selected and regenerated. Preferably, transformed cells are first identified using a selection marker simultaneously introduced into the host cells along with the DNA construct of the present invention. The most widely used reporter gene for gene fusion experiments has been uidA, a gene from *Escherichia coli* that encodes the β-glucuronidase protein, also known as GUS. Jefferson et al., "GUS Fusions: β Glucuronidase as a Sensitive and Versatile Gene Fusion Marker in Higher Plants," *EMBO Journal* 6:3901–3907 (1987), which is hereby incorporated by reference. GUS is a 68.2 kd protein that acts as a tetramer in its native form. It does not require cofactors or special ionic conditions, although it can be inhibited by divalent cations like $Cu^{2+}$ or $Zn^{2+}$. GUS is active in the presence of thiol reducing agents like β-mercaptoethanol or dithiothreitol (DTT).

In order to evaluate GUS activity, several substrates are available. The most commonly used are 5 bromo-4 chloro-3 indolyl glucuronide (X-Gluc) and 4 methyl-umbelliferyl-glucuronide (MUG). The reaction with X-Gluc generates a blue color that is useful in histochemical detection of the gene activity. For quantification purposes, MUG is preferred, because the umbelliferyl radical emits fluorescence under UV stimulation, thus providing better sensitivity and easy measurement by fluorometry (Jefferson et al., "GUS Fusions: β Glucuronidase as a Sensitive and Versatile Gene Fusion Marker in Higher Plants," *EMBO Journal* 6:3901–3907 (1987), which is hereby incorporated by reference). Other suitable selection markers include, without limitation, markers encoding for antibiotic resistance, such as the nptII gene which confers kanamycin resistance (Fraley, et al., *Proc. Natl. Acad. Sci. USA,* 80:4803–4807 (1983), which is hereby incorporated by reference) and the dhfr gene, which confers resistance to methotrexate (Bourouis et al., *EMBO J.* 2:1099–1104 (1983), which is hereby incorporated by reference). A number of antibiotic-resistance markers are known in the art and others are continually being identified. Any known antibiotic-resistance marker can be used to transform and select transformed host cells in accordance with the present invention. Cells or tissues are grown on a selection medium containing an antibiotic, whereby generally only those transformants expressing the antibiotic resistance marker continue to grow. Similarly, enzymes providing for production of a compound identifiable by luminescence, such as luciferase, are useful. The selection marker employed will depend on the target species; for certain target species, different antibiotics, herbicide, or biosynthesis selection markers are preferred.

Once a recombinant plant cell or tissue has been obtained, it is possible to regenerate a full-grown plant therefrom. Means for regeneration vary from species to species of plants, but generally a suspension of transformed protoplasts or a petri plate containing transformed explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

Plant regeneration from cultured protoplasts is described in Evans, et al., *Handbook of Plant Cell Cultures. Vol. 1:* (MacMillan Publishing Co., New York, 1983); and Vasil I. R. (ed.), *Cell Culture and Somatic Cell Genetics of Plants,* Acad. Press, Orlando, Vol. I, 1984, and Vol. III (1986), which are hereby incorporated by reference.

It is known that practically all plants can be regenerated from cultured cells or tissues, including but not limited to, all major species of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery, carrot, squash, pumpkin, zucchini, cucumber, apple, pear, melon, strawberry, grape, raspberry, pineapple, soybean, tobacco, tomato, sorghum, sugarcane, and non-fruit bearing trees such as poplar, rubber, Paulownia, pine, and elm.

After the DNA construct is stably incorporated in transgenic plants, it can be transferred to other plants by sexual crossing or by preparing cultivars. With respect to sexual crossing, any of a number of standard breeding techniques can be used depending upon the species to be crossed. Cultivars can be propagated in accord with common agricultural procedures known to those in the field. Alternatively, transgenic seeds are recovered from the transgenic plants. The seeds can then be planted in the soil and cultivated using conventional procedures to produce transgenic plants.

Since loss of function (Sin1 mutation) delays flowering, a gain of function, for example, by overexpression of Sin1 gene, should promote early flowering. Accordingly, another aspect of the present invention relates to a method of increasing fertility in plants by transforming plants with the nucleic acid of the present invention. Fertility can be functionally (albeit simplistically) defined as the onset of reproductive maturity. By reducing the time from vegetative to floral stage in plants, overall breeding time can be reduced.

Thus, the nucleic acid molecule of the present invention, as a regulator of flowering time, can be used to accelerate flowering in plants. This involves transforming plants with the nucleic acid of the present invention in an expression vector as described above, operably linked to an inducible promoter, such as the glucocorticoid inducible promoter. Transgenic plants in which an inducible promoter is present are treated with the suitable inducing agent (e.g., dexamethasone for the glucocorticoid inducible promoter) to induce flowering. Inducing SIN1 protein expression earlier in the development of the plant than normal accelerates early flowering, such that breeding time can be reduced. In addition, induction of flowering eliminates dependence upon external factors for flowering such as temperature and light (Coupland G., "Genetic and Environmental Control of Flowering Time in Arabidopsis," *Mol. Gen. Genet.* 242:81–89 (1995), which is hereby incorporated by reference), which are beyond the control of the average farmer. Early flowering plant lines may be especially useful for cultivation in short daylight environments.

In another aspect of the present invention, the fecundity of plants can be increased by overexpression of the nucleic acid of the present invention, under control of a constitutive promoter. Fecundity relates to reproductive maturity in combination with the total number of seeds a mature plant can produce. Thus, decreasing the time to flowering with expression of the protein of the present invention is one factor of increased fecundity, as it increases time spent in the adult phase. The other factor, seed development, is also related to expression of the protein of the present invention, as this protein, when maternally expressed, appears to coordinate the expression of zygotic pattern formation in the embryo. In this aspect of the present invention, the nucleic acid of the present invention is inserted into an expression vector, as described above, operably linked to a constitutive promoter, for example, the CaMV35S promoter. Increased expression of the protein of the present invention, which functions both in the formation of seeds and in the mother plant in embryo formation, can result in increased fecundity.

The present invention also relates to a method of decreasing fertility in plants. Because it may be commercially desirable to produce sterile female progeny, or plants with low expression of the protein of the present invention, transgenic plants can be produced in which the expression of this protein is down-regulated, or even entirely "switched off." In one aspect of the present invention, the nucleic acid of the present invention is replaced in the above-described expression vector by an antisense nucleic acid molecule which is complementary to the nucleic acid of the present invention or a fragment thereof. Antisense technology is commonplace to those skilled in the art, and the preparation of a vector and transgenic plants containing an antisense nucleic acid would be followed as described above. Transgenic plants are produced as described above, which exhibit a phenotype deficient in the nucleic acid of the present invention.

In another aspect of the present invention, the silencing of the constitutive SIN1 gene involves the use of double-stranded RNA ("dsRNA") interference ("RNAi"), a procedure which has recently been shown to induce potent and specific post-translational gene silencing in many organisms. See Bosher et al., "RNA Interference: Genetic Wand and Genetic Watchdog," *Nat Cell Biol* 2:E31–6 (2000); Tavernarakis et al., "Heritable and Inducible Genetic Interference by Double-Stranded RNA encoded by Transgenes," *Nat Genetics* 24:180–3 (2000), which are hereby incorporated by reference. To construct transformation vectors that produce RNAs capable of duplex formation, two nucleic acid sequences according to the present invention, one in the sense and the other in the antisense orientation, are operably linked, and placed under the control of a strong viral promoter, such as CaMV 35S. The construct is introduced into the genome of *Arabidopsis thaliana* by Agrobacterium-mediated transformation (Chuang et al., "Specific and Heritable Genetic Interference by Double-Stranded RNA in *Arabidopsis thaliana*," *Proc. Natl. Acad. Sci. USA* 97:4985–90 (2000), which is hereby incorporated by reference), causing specific and heritable genetic interference, as evidenced by SIN1 deficient phenotype.

In another aspect of the present invention, plant lines containing insertional mutations are produced, disrupting the endogenous SIN1 gene and thereby creating a SIN1 protein deficient plant with decreased fertility. This is accomplished by making use of well-characterized plant transposons such as the maize Activator ("Ac") and Dissociation ("Ds") family of transposable elements. The family is comprised of the autonomous element Ac, and the non-autonomous Ds element. Ds elements are not capable of autonomous transposition, but can be trans-activated to transpose by Ac. Hehl et al., "Induced Transposition of Ds by a Stable Ac in Crosses of Transgenic Tobacco Plants," *Mol. Gen. Genet.* 217:53–59 (1989), which is hereby incorporated by reference. Thus, transposable elements, such as Ac/Ds of maize, can be operably linked to the nucleic acid of the present invention, transferred to other plants to generate a relatively small number if anchor plants (such as 500), and then to produce a much larger number of secondary insertional-mutant plant lines. The Ac/Ds system has been improved by the use of enhancer- and gene-trap plasmids (Sundaresan et al., "Patterns of Gene Action in Plant Development Revealed by Enhancer Trap and Gene Trap Transposable Elements," *Genes & Develop.* 9:1797–1810 (1995), which is hereby incorporated by reference), which allow disrupted genes with no phenotype to be detected by expression of a reporter gene (such as Gus). After insertion of the mutant genes, plants are screened using marker genes and appropriate crosses made to produce stable mutant plant lines. Sundaresan et al., "Patterns of Gene Action in Plant Development Revealed by Enhancer Trap and Gene Trap Transposable Elements," *Genes & Develop.* 9:1797–1810 (1995), which is hereby incorporated by reference.

In another aspect of the present invention, the point mutations identified herein which result in SIN1 deficient phenotypes sus1, sin1-1, and sin1-2 can be prepared and used in the construct of the present invention to create transgenic plants and seeds carrying these point mutation alleles. The sus1 mutation is predicted to delete most of the functional domains of the SIN1 protein. The sin1-1 mutation produces a 415-proline to serine change in the protein; the sin1-2 produces a 431-isoleucine to lysine change within the C-terminus helicase domain. Molecular modeling indicates that these two mutations perturb the RNA binding face of the DEHX box of the helicase C domain. Homozygous sin1-1 or sin1-2 mutation in Arabidopsis causes female sterility due to two separate phenotypic defects, and sinl mutants are late flowering. The allelic DNA can be synthetically produced, according to methods known to those in the art, or by inserting the above disclosed point mutations in the nucleic acid of the present invention, thereby creating plants with decreased fertility and decreased/late flowering.

In various aspects of the present invention the SIN1 gene is either up- or down-regulated, or turned off entirely. In order to ascertain the increase or decrease in SIN1 protein expression resulting from genetic manipulation, measurement of the production of the SIN1 protein in plant tissues is carried out following transformation. Western blot, or any similar method of protein detection is appropriate, using either polyclonal or monoclonal antibodies to the protein of the present invention. Polyclonal antibodies can be produced by procedures well-known to those skilled in the art, such as those disclosed in E. Harlow, et al, editors *Antibodies: A Laboratory Manual* (1988), which is hereby incorporated by reference. The preparation of monoclonal antibodies, as well as Fab and F(ab')2 fragments, also useful in protein detection methods, can be produced by various commonly used methods, such as those described in Goding, *Monoclonal Antibodies: Principles and Practice*, pp. 98–118, New York: Academic Press (1983), which is hereby incorporated by reference.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated nucleic acid molecule encoding a short integuments1 protein, wherein the nucleic acid molecule either. 1) has a nucleotide sequence of SEQ ID NO: 1 or 2) encodes a protein having an amino acid sequence of SEQ ID NO: 2.

2. An isolated nucleic acid molecule according to claim 1, wherein the nucleic acid molecule encodes a protein having at amino acid sequence of SEQ ID NO: 2.

3. An isolated nucleic acid molecule according to claim 1, wherein the nucleic acid molecule has a nucleotide sequence of SEQ ID NO: 1.

4. An antisense nucleic acid molecule encoding a nucleic acid sequence which is complementary to the nucleic acid molecule according to claim 1.

5. An expression vector comprising a transcriptional and translational regulatory DNA operably linked to the nucleic acid molecule according to claim 1.

6. An expression vector according to claim 5, wherein the nucleic acid molecule is in proper sense of orientation and correct reading frame.

7. A host cell transformed with the nucleic acid molecule according to claim 1.

8. A host cell according to claim 7, wherein the cell is selected from a group consisting of a bacterial cell, a virus, a yeast cell, and a plant cell.

9. A transgenic plant transformed with the nucleic acid molecule according to claim 1.

10. A transgenic plant seed transformed with the nucleic acid molecule according to claim 1.

11. A method of increasing flowering in a plant comprising:

transforming the plant with the nucleic acid molecule according to claim 1 under conditions effective to increase flowering in the plant.

12. A method of increasing fertility in a plant comprising:

transforming the plant with the nucleic acid molecule according to claim 1 under conditions effective to increase fertility in the plant.

13. A method of increasing fecundity of a plant comprising:

transforming the plant with the nucleic acid molecule according to claim 1 under conditions effective to increase fecundity of the plant.

14. A method decreasing fertility in a plant comprising:

transforming the plant with a nucleic acid molecule that either: 1) has a nucleotide sequence of SEQ ID NO: 1 or 2) encodes a protein having an amino acid sequence of SEQ ID NO: 2 wherein the nucleic acid molecule of 1) or 2) has a nucleotide mutation characterized by either a) a single C to T transition resulting in an amino acid change of 415-proline of SEQ ID NO: 2 to serine or b) a single T or A transversion resulting in an amino acid change of 431-isoleucine SEQ ID NO: 2 to lysine under conditions effective to decrease fertility in the plant.

* * * * *